United States Patent
Serrano Sanmiguel et al.

(10) Patent No.: US 9,241,887 B2
(45) Date of Patent: Jan. 26, 2016

(54) SYSTEMS AND METHODS FOR SKIN REJUVENATION

(71) Applicant: Sesvalia USA, LLC, Davie, FL (US)

(72) Inventors: Gabriel Serrano Sanmiguel, Atlanta, GA (US); Juan Manuel Serrano Nunez, Puzol (ES); Joaquin Melendez Zamora, Massamagrell (ES)

(73) Assignee: Sesvalia USA, LLC, Davie, FL (US)

( * ) Notice: Subject to any disclaimer, the term of this patent is extended or adjusted under 35 U.S.C. 154(b) by 0 days.

(21) Appl. No.: 13/987,708

(22) Filed: Aug. 23, 2013

(65) Prior Publication Data
US 2013/0345307 A1    Dec. 26, 2013

Related U.S. Application Data

(63) Continuation of application No. 12/798,416, filed on Apr. 2, 2010, now Pat. No. 8,568,749.

(60) Provisional application No. 61/166,192, filed on Apr. 2, 2009, provisional application No. 61/166,165, filed on Apr. 2, 2009.

(51) Int. Cl.
*A61K 8/365* (2006.01)
*A61K 8/14* (2006.01)
(Continued)

(52) U.S. Cl.
CPC . *A61K 8/365* (2013.01); *A61K 8/14* (2013.01); *A61K 8/342* (2013.01); *A61K 8/35* (2013.01);
(Continued)

(58) Field of Classification Search
None
See application file for complete search history.

(56) References Cited

U.S. PATENT DOCUMENTS

| 4,235,871 | A  | 11/1980 | Papahadjopoulos et al. |
| 6,710,076 | B2 | 3/2004  | Ancira |

(Continued)

FOREIGN PATENT DOCUMENTS

| EP | 1837056 | 9/2007 |
| EP | 2236129 | 10/2010 |

(Continued)

OTHER PUBLICATIONS

Bitter, "Noninvasive Rejuvenation of Photodamaged Skin Using Serial, Full-Face Intense Pulsed Light Treatments" (abstract), Dermatologic Surgery, 26(9), pp. 835-843 (Sep. 2000).*

(Continued)

*Primary Examiner* — Bethany Barham
*Assistant Examiner* — Barbara Frazier
(74) *Attorney, Agent, or Firm* — Greenberg Traurig, LLP; Daivd J. Dykeman; Natalie Salem

(57) ABSTRACT

Systems and methods for skin rejuvenation are disclosed herein. In an embodiment, a skin rejuvenation system includes a unit dose of a booster product that includes active ingredients of ferulic acid and phloretin; a unit dose of at least one exfoliating product that includes active ingredients of ferulic acid and phloretin in combination with fruit acids or alpha hydroxyacids; and a unit dose of a nano-additive product for enhancing penetration of the active ingredients. A method for skin rejuvenation includes applying topically, to a skin surface to be treated, a booster product including active ingredients of ferulic acid and phloretin; applying topically, to the skin surface, at least one exfoliating product including active ingredients of ferulic acid and phloretin in combination with one of fruit acids or alpha hydroxyacids; and applying topically, to the skin surface, a nano-additive product for enhancing penetration of the active ingredients.

21 Claims, 8 Drawing Sheets
(8 of 8 Drawing Sheet(s) Filed in Color)

(51) Int. Cl.

| | | |
|---|---|---|
| A61K 8/35 | (2006.01) | |
| A61Q 19/00 | (2006.01) | |
| A61Q 19/02 | (2006.01) | |
| A61Q 19/08 | (2006.01) | |
| A61Q 19/10 | (2006.01) | |
| A61K 8/34 | (2006.01) | |
| A61K 8/36 | (2006.01) | |
| A61K 8/362 | (2006.01) | |
| A61K 8/42 | (2006.01) | |
| A61K 8/49 | (2006.01) | |
| A61K 8/60 | (2006.01) | |
| A61Q 17/00 | (2006.01) | |

(52) U.S. Cl.
CPC . *A61K 8/36* (2013.01); *A61K 8/362* (2013.01); *A61K 8/42* (2013.01); *A61K 8/4926* (2013.01); *A61K 8/60* (2013.01); *A61Q 17/00* (2013.01); *A61Q 19/00* (2013.01); *A61Q 19/02* (2013.01); *A61Q 19/08* (2013.01); *A61Q 19/10* (2013.01); *A61K 2800/28* (2013.01); *A61K 2800/413* (2013.01); *A61K 2800/88* (2013.01)

(56) References Cited

U.S. PATENT DOCUMENTS

| | | | |
|---|---|---|---|
| 6,869,611 | B1 | 3/2005 | Kligman et al. |
| 7,404,967 | B2 | 7/2008 | Hahn et al. |
| 8,568,749 | B2 | 10/2013 | Sanmiguel et al. |
| 2002/0127256 | A1 | 9/2002 | Murad |
| 2004/0265366 | A1 | 12/2004 | Pareja et al. |
| 2007/0154419 | A1 | 7/2007 | Hattendorf et al. |
| 2007/0225360 | A1 | 9/2007 | Pinnell et al. |
| 2009/0137534 | A1 | 5/2009 | Chaudhuri |
| 2010/0255079 | A1 | 10/2010 | Sanmiguel et al. |
| 2010/0255080 | A1 | 10/2010 | Sanmiguel et al. |

FOREIGN PATENT DOCUMENTS

| | | |
|---|---|---|
| EP | 2241303 | 10/2010 |
| GB | 2015464 | 9/1979 |
| JP | H04 235112 | 8/1992 |
| JP | H06 256137 | 9/1994 |
| JP | 03/212774 | 7/2003 |
| WO | 01/07004 | 2/2001 |
| WO | WO 02/13788 | 2/2002 |
| WO | 2005/102373 | 11/2005 |
| WO | 2008/002347 | 1/2008 |

OTHER PUBLICATIONS

Akaraphanth et al., "Efficacy of ALA-PDT vs. Blue Light in the Treatment of Acne," *Photodermatol Photoimmunol Photomed*, 23(5), pp. 186-190 (Oct. 2007).

van den Akker et al., "Chapter 4: Protoporphyrin IX Fluorescence Kinetics and Localization after Topical Application of ALA Pentyl Ester and ALA on Hairless Mouse Skin with UVB-Induced Early Skin Cancer," in *In Vivo and In Vitro Studies on the Localisation and Kinetics of Porphyrin Related Drugs for Photodetection and Photodynamic Therapy*, Doctoral Thesis, Erasmus Universiteit Rotterdam, pp. 54-68 (Nov. 2003).

Al-Sereitia et al., "Pharmacology of Rosemary (*Rosmarinus officinalis* Linn.) and its Therapeutic Potentials," *Indian Journal of Experimental Biology*, 37, pp. 124-131 (Feb. 1999).

Alster et al., "Photorejuvenation of Facial Skin with Topical 20% 5-Aminolevulinic Acid and Intense Pulsed Light Treatment: A Split-Face Comparison Study," *Journal of Drugs in Dermatology*, 4(1), pp. 35-38 (Jan.-Feb. 2005).

Auner et al., "Influence of Phloretin on the Skin Permeation of Lidocaine from Semisolid Preparations," *European Journal of Pharmaceutics and Biopharmaceutics*, 57(2), pp. 307-312 (Mar. 2004).

Auner et al., "Interaction of Phloretin and 6-Ketocholestanol with DPPC-Liposomes as Phospholipid Model Membranes," *International Journal of Pharmacy*, 294(1-2), pp. 149-155 (Apr. 27, 2005).

Avram et al., "Effectiveness and Safety of ALA-IPL in Treating Actinic Keratosees and Photodamage," *J Drugs Dermatol*, 3(1 Suppl), pp. S32-S39 (Jan.-Feb. 2004).

Bissonette et al., "Large Surface Photodynamic Therapy with Aminolevulinic Acid: Treatment of Actinic Keratoses and Beyond," *J Drugs Dermatol*, 3(1 Suppl), pp. S26-S31 (Jan.-Feb. 2004).

Bjerring et al., "Skin Fluorescence Controlled Photodynamic Photorejuvenation (Wrinkle Reduction)," *Lasers in Surgery and Medicine*, 41(5), pp. 327-336 (Jul. 2009).

Borutaite et al., "Mitochondrial Regulation of Caspase Activation by Cytochrome Oxidase and Tetramethylphenylenediamine via Cytosolic Cytochrome *c* Redox State," *The Journal of Biological Chemistry*, 282(43), pp. 31124-31130 (Oct. 26, 2007).

Brown et al., "The Present and Future Role of Photodynamic Therapy in Cancer Treatment," *The Lancet Oncology*, 5, pp. 497-508 (Aug. 2004).

Burgess, "Topical Vitamins," *Journal of Drugs in Dermatology*, 7(Supp.), pp. s2-s6 (Jul. 2008).

Burgess, "Chapter 70: Cosmetic Products" in *Dermatology for Skin of Color*, eds. A. Paul Kelly and Susan Taylor, Edition 1, pp. 18-30 (Apr. 8, 2009).

Burke, "Interaction of Vitamins C and E as Better Cosmeceuticals," *Dermatologic Therapy*, 20(5), pp. 314-321 (Sep.-Oct. 2007).

Casas et al., "ALA and ALA Hexyl Ester in Free and Liposomal Formulations for the Photosensitisation of Tumour Organ Cultures," *British Journal of Cancer*, 86(5), pp. 837-842 (Mar. 4, 2002).

Casas et al., "The Influence of the Vehicle on the Synthesis of Porphyrins After Topical Application of 5-Aminolaevulinic Acid. Implications in Cutaneous Photodynamic Sensitization," *British Journal of Dermatology*, 143(3), pp. 564-572 (Sep. 2000).

Casas et al., "Aminolevulinic Acid Derivatives and Liposome Delivery as Strategies for Improving 5-Aminolevulinic Acid-Mediated Photodynamic Therapy," *Current Medicinal Chemistry*, 13(10), pp. 1157-1168 (2006).

Christiansen et al., "5-ALA for Photodynamic Photorejuvenation—Optimization of Treatment Regime Based on Normal-Skin Fluorescence Measurements," *Lasers in Surgery and Medicine*, 39(4), pp. 302-310 (Apr. 2007).

Darr et al., "Topical Vitamin C Protects Porcine Skin from Ultraviolet Radiation-induced Damage," *British Journal of Dermatology*, 127(3), pp. 247-253 (Sep. 1992).

Darr et al., "Effectiveness of Antioxidants (Vitamin C and E) With and Without Sunscreens as Topical Photoprotectants," *Acta Derm Venereol (Stockh)*, 76(4), pp. 264-268 (Jul. 1996).

Di Venosa et al., "Characterisation of Liposomes Containing Aminolevulinic Acid and Derived Esters," *Journal of Photochemistry and Photobiology B: Biology*, 92, pp. 1-9 (Apr. 7, 2008).

Dover et al., "Topical 5-Aminolevulinic Acid Combined with Intense Pulsed Light in the Treatment of Photoaging," *Archives of Dermatology*, 141(10), pp. 1247-1252 (Oct. 2005).

Edlich et al., "Photoprotection by Sunscreens with Topical Antioxidants and Systemic Antioxidants to Reduce Sun Exposure," *Journal of Long-Term Effects of Medical Implants*, 14(4), pp. 317-340 (2004).

Fang et al., "Comparison of 5-Aminolevulinic Acid-Encapsulated Liposome Versus Ethosome for Skin Delivery for Photodynamic Therapy," *International Journal of Pharmaceutics*, 356(1-2), pp. 144-152 (May 22, 2008).

Fang et al., "Physicochemical and Safety Evaluation of 5-Aminolevulinic Acid in Novel Liposomes as Carrier for Skin Delivery," *Journal of Liposome Research*, 18(1), pp. 31-45 (2008).

Freedman, "Topical Polyphenolic Antioxidants Reduce the Adverse Effects of Intense Pulsed Light Therapy," *Journal of Cosmetic and Laser Therapy*, 11(3), pp. 142-145 (Sep. 2009).

Freedman, "Topical Antioxidant Application Augments the Effects of Intense Pulsed Light Therapy," *Journal of Cosmetic Dermatology*, 8(4), pp. 254-259 (Dec. 2009).

Godal et al., "New Derivatives of 5-Aminolevulinic Acid for Photodynamic Therapy: Chemical Synthesis and Porphyrin Produc-

(56) References Cited

OTHER PUBLICATIONS tion in In Vitro and In Vivo Biological Systems," *Journal of Environmental Pathology, Toxicology, and Oncology*, 25(1-2), pp. 109-126 (2006).
Gold et al., "ALA-PDT and Blue Light Therapy for Hidradenitis Suppurative," *Journal of Drugs in Dermatology*, 3(1), pp. S32-S35 (Jan.-Feb. 2004).
Gold et al., "Split-Face Comparison of Photodynamic Therapy with 5-Aminolevulinic Acid and Intense Pulsed Light Versus Intense Pulsed Light Alone for Photodamage," *Dermatologic Surgery*, 32(6), pp. 795-801 (Jun. 2006).
Gold et al., "Treatment of Moderate to Severe Inflammatory Acne Vulgaris: Photodynamic Therapy with 5-Aminolevulinic Acid and a Novel Advanced Fluorescence Technology Pulsed Light Source," *Journal of Drugs in Dermatology*, 6(3), pp. 319-322 (Mar. 2007).
Haedersdal et al., "Evidence-Based Review of Lasers, Light Sources and Photodynamic Therapy in the Treatment of Acne Vulgaris," *JEADV*, 22(3), pp. 267-278 (Mar. 2008).
Hall et al., "Dose Response of Combination Photorejuvenation Using Intense Pulsed Light-Activated Photodynamic Therapy and Radiofrequency Energy," *Archives of Facial Plastic Surgery*, 6(6), pp. 374-378 (Nov.-Dec. 2004).
Han et al., "Expression Pattern and Intensity of Protoporphyrin IX Induced by Liposomal 5-Aminolevulinic Acid in Rat Pilosebaceous Unit Throughout Hair Cycle," *Archives for Dermatological Research*, 297(5), pp. 210-217 (Nov. 2005).
Hong et al., "Topical Aminolevulinic Acid-Photodynamic Therapy for the Treatment of Acne Vulgaris," *Photodermatology, Photoimmunology & Photomedicine*, 21(6), pp. 322-325 (Dec. 2005).
Hongcharu et al., "Topical ALA-Photodynamic Therapy for the Treatment of Acne Vulgaris," *Journal of Investigative Dermatology*, 115(2), pp. 183-192 (Aug. 2000).
Hwang et al., "Topical Photodynamic Therapy for Treatment of Acne Vulgaris: Comparison of Short and Long Pulse Durations," *Free Communications: Laser Therapy*, Presented at the 15th Congress of the European Academy of Dermatology and Venereology, Rhodes, Greece (Oct. 4-7, 2006).
Hwang et al., "Topical Photodynamic Therapy for Treatment of Acne Vulgaris: Comparison of Two IIPL Applicators and Two Application Times of ALA," *Modelo Clinic* (2006), accessed at <www.ellipse.org/ref.aspx?id=1225>.
Iiyama et al., "Covalent Cross-Links in the Cell Wall," *Plant Physiology*, 104(2), pp. 315-320 (Feb. 1994).
Ishikado et al., "Liposomal Lactoferrin Induced Significant Increase of the Interferon-Alpha (IFN-α) Producibility in Healthy Volunteers," *BioFactors*, 21(1-4), pp. 69-72 (2004).
Jonsson et al., "Tissue Oxygenation, Anemia, and Perfusion in Relation to Wound Healing in Surgical Patients," *Annals of Surgery*, 214(5), pp. 605-613 (Nov. 1991).
Kampa et al., "Antiproliferative and Apoptotic Effects of Selective Phenolic Acids on T47D Human Breast Cancer Cells: Potential Mechanisms of Action," *Breast Cancer Research*, 6(2), pp. R63-R74 (Dec. 15, 2003).
Katz et al., "Photodynamic Therapy for the Treatment of Erythema, Papules, Pustules, and Severe Flushing Consistent with Rosacea," *Journal of Drugs in Dermatology*, 5(2), pp. 6-8 (Feb. 2006).
Katz et al., "Efficacy of Microdermabrasion Preceding ALA Application in Reducing the Incubation Time of ALA in Laser PDT," *Journal of Drugs in Dermatology*, 6(2), pp. 140-142 (Feb. 2007).
Kaufman et al., "The Microclimate Chamber: Morphological Aspects of Experimental Deep Burns Treated Topically with Continuous Humidified Oxygen," *Annals of Plastic Surgery*, 10(3), pp. 218-223 (Mar. 1983).
Kaufman, "Shining the Light on PDT Advancements," *Practical Dermatology*, pp. 36-39 (Jun. 2008).
Kemmner et al., "Silencing of Human Ferrochelatase Causes Abundant Protoporphyrin-IX Accumulation in Colon Cancer," *The FASEB Journal*, 22, pp. 500-509 (Feb. 2008).
Kosobe et al., "Size and Surface Charge Effect of 5-Aminolevulinic Acid-Containing Liposomes on Photodynamic Therapy for Cultivated Cancer Cells," *Drug Development and Industrial Pharmacy*, 31(7), pp. 623-629 (Aug. 2005).
Lee, "Role of NADPH Oxidase-Mediated Generation of Reactive Oxygen Species in the Mechanism of Apoptosis Induced by Phenolic Acids in HepG2 Human Hepatoma Cells," *Archives of Pharmacal Research*, 28(10), pp. 1183-1189 (Oct. 2005).
Lesca, "Protective Effects of Ellagic Acid and Other Plant Phenols on Benzo[a]pyrene-Induced Neoplasia in Mice," *Carcinogenesis*, 4(12), pp. 1651-1653 (Dec. 1983).
Lin et al., "Ferulic Acid Stabilizes a Solution of Vitamins C and E and Doubles its Photoprotection of Skin," *The Journal of Investigative Dermatology*, 125, pp. 826-832 (Oct. 4, 2005).
Lin et al., "UV Photoprotection by Combination Topical Antioxidants Vitamin C and Vitamin E," *Journal of the American Academy of Dermatology*, 48(6), pp. 866-874 (Jun. 2003).
Lopez et al., "Iontophoretic Delivery of 5-Aminolevulinic Acid (ALA): Effect of pH," *Pharmaceutical Research*, 18(3), pp. 311-315 (Mar. 2001).
Marmur et al., "Ultrastructural Changes Seen After ALA-IPL Photorejuvenation: A Pilot Study," *Journal of Cosmetic and Laser Therapy*, 7(1), pp. 21-24 (Mar. 2005).
Mathew et al., "Ferulic Acid: An Antioxidant Found Naturally in Plant Cell Walls and Feruloyl Esterases Involved in its Release and Their Applications," *Critical Reviews in Biotechnology*, 24(2-3), pp. 59-83 (Jan. 2004).
Merclin et al., "Transdermal Delivery from a Lipid Sponge Phase—Iontophoretic and Passive Transport In Vitro of 5-Aminolevulinic Acid and its Methyl Ester," *Journal of Controlled Release*, 100(2), pp. 191-198 (Nov. 24, 2004).
Miah, "ALA-based Photodynamic Therapy of Jurkat Cells: Temperature Dependence," *Pakistan Journal of Biological Sciences*, 5(7), pp. 770-773 (2002).
Moan et al., "Chapter 1: An Outline of the History of PDT," in *Photodynamic Therapy*, ed. Thierry Patrice, Edition 1, pp. 1-17 (Apr. 26, 2003).
Mori et al., "Chemopreventive Effects of Ferulic Acid on Oral and Rice Germ on Large Bowel Carcinogenesis," *Anticancer Research*, 19(5A), pp. 3775-3778 (Sep.-Oct. 1999).
Monsky et al., "Radio-frequency Ablation Increases Intratumoral Liposomal Doxorubicin Accumulation in a Rat Breast Tumor Model," *Radiology*, 224(3), pp. 823-829 (Sep. 2002).
Navickiene, "Photodynamic Diagnostics of Skin and Mucosal Lesions," *ACTA Medica Lituanica*, 14(2), pp. 99-103 (2007).
Nestor et al., "The Use of Photodynamic Therapy in Dermatology: Results of a Consensus Conference," *Journal of Drugs in Dermatology*, 5(2), pp. 140-154 (Feb. 2006).
Olthof et al., "Chlorogenic Acid and Caffeic Acid Are Absorbed in Humans," *The Journal of Nutrition*, 131(1), pp. 66-71 (Jan. 1, 2001).
Oo et al., "5-Aminolevulinic Acid-conjugated Gold Nanoparticles for Photodynamic Therapy of Cancer," *Nanomedicine*, 3(6), pp. 777-786 (Dec. 2008).
Oresajo et al., "Protective Effects of a Topical Antioxidant Mixture Containing Vitamin C, Ferulic Acid, and Phloretin Against Ultraviolet-induced Photodamage in Human Skin," *Journal of Cosmetic Dermatology*, 7(4), pp. 290-297 (Dec. 2008).
Osakabe et al., "Anti-inflammatory and Anti-allergic Effect of Rosmarinic Acid (RA); Inhibition of Seasonal Allergic Rhinoconjunctivitis (SAR) and its Mechanism," *BioFactors*, 21(1-4), pp. 127-131 (2004).
Padayatty et al., "Vitamin C as an Antioxidant: Evaluation of its Role in Disease Prevention," *Journal of the American College of Nutrition*, 22(1), pp. 18-35 (Feb. 2003).
Peyrat-Maillard et al., "Antioxidant Activity of Phenolic Compounds in 2,2'-Azobs (2-Amidinopropane) Dihydrochloride (AAPH)-Induced Oxidation: Synergistic and Antagonistic Effects," *Journal of the American Oil Chemists' Society*, 80(10), pp. 1007-1012 (Oct. 2003).
Pierre et al., "Stratum Corneum Lipids Liposomes for the Topical Delivery of 5-Aminolevulinic Acid in Photodynamic Therapy of Skin Cancer: Preparation and In Vitro Permeation Study," *BMC Dermatology*, 1(5), pp. 1-6 (Aug. 30, 2001).

(56) References Cited

OTHER PUBLICATIONS

Pinnell, "Cutaneous Photodamage, Oxidative Stress, and Topical Antioxidant Protection," *Journal of the American Academy of Dermatology*, 48(1), pp. 1-19 (Jan. 2003).

Planas et al., "Protective Effect of Fructose 1,6-bisphosphate Against Carrageenan-Induced Inflammation," *European Journal of Pharmacology*, 237(2-3), pp. 251-255 (Jun. 24, 1993).

Pollock et al., "Topical Aminolaevulinic Acid-Photodynamic Therapy for the Treatment of Acne Vulgaris: A Study of Clinical Efficacy and Mechanism of Action," *British Journal of Dermatology*, 151(3), pp. 616-622 (Sep. 2004).

Poquet et al., "Transport and Metabolism of Ferulic Acid through the Colonic Epithelium," *Drug Metabolism and Disposition*, 36(1), pp. 190-197 (Jan. 2008).

Psotova et al., "Photoprotective Properties of *Prunella vulgaris* and Rosmarinic Acid on Human Keratinocytes," *Journal of Photochemistry and Photobiology B: Biology*, 84(3), pp. 167-174 (Sep. 1, 2006).

Riaz, "Liposomes Preparation Methods," *Pakistan Journal of Pharmaceutical Sciences*, 19(1), pp. 65-77 (Jan. 1996).

Rice-Evans et al., "Structure-Antioxidant Activity Relationships of Flavonoids and Phenolic Acids," *Free Radical Biology and Medicine*, 20(7), pp. 933-956 (1996).

Rojanamatin et al., "Treatment of Inflammatory Facial Acne Vulgaris with Intense Pulsed Light and Short Contact of Topical 5-Aminolevulinic Acid: A Pilot Study," *Dermatologic Surgery*, 32(8), pp. 991-997 (Aug. 2006).

Rozman et al., "Stability of Vitamins C and E in Topical Microemulsions for Combined Antioxidant Therapy," *Drug Delivery*, 14(4), pp. 235-245 (Apr. 2007).

Ruiz-Rodriguez et al., "Photodynamic Photorejuvenation," *Dermatologic Surgery*, 28(8), pp. 742-744 (Aug. 2002).

Ruiz-Rodriguez et al., "Enhanced Efficacy of Photodynamic Therapy after Fractional Resurfacing: Fractional Photodynamic Rejuvenation," *Journal of Drugs in Dermatology*, 6(8), pp. 818-820 (Aug. 2007).

Ryou et al., "Acne-photodynamic Therapy with Intra-lesional Injection of 5-aminolevulinic Acid," *Photodermatology, Photoimmunology & Photomedicine*, 25(1), pp. 57-58 (Feb. 2009).

Santos et al., "Effectiveness of Photodynamic Therapy with Topical 5-Aminolevulinic Acid and Intense Pulsed Light Versus Intense Pulsed Light Alone in the Treatment of Acne Vulgaris: Comparative Study," *Dermatologic Surgery*, 31(8 Pt. 1), pp. 910-915 (Aug. 2005).

Scott, "Oxygen and the Connective Tissues," *Trends in Biochemical Sciences*, 17(9), pp. 340-343 (Sep. 1, 1992).

Serrano et al., "Photodynamic Therapy with Low-Strength ALA, Repeated Applications and Short Contact Periods (40-60 Minutes) in Acne, Photoaging and Vitiligo," *Journal of Drugs in Dermatology*, 8(6), pp. 562-568 (Jun. 2009).

Shao et al., "Apple Polyphenols, Phloretin and Phloridzin: New Trapping Agents of Reactive Dicarbonyl Species," *Chemical Research in Toxicology*, 21(10), pp. 2042-2050 (Oct. 2008).

Svobodová et al., "Natural Phenolics in the Prevention of UV-Induced Skin Damage: A Review," *Biomeical Papers*, 147(2), pp. 137-145 (Dec. 2003).

Taub, "A Comparison of Intense Pulsed Light, Combination Radiofrequency and Intense Pulsed light, and Blue Light in Photodynamic Therapy for Acne Vulgaris," *Journal of Drugs in Dermatology*, 6(10), pp. 1010-1016 (Oct. 2007).

Verkman et al., "Kinetics of Phloretin Binding to Phosphatidylcholine Vesicle Membranes," *J. Gen. Physiol.*, 75, pp. 673-692 (Jun. 1980).

Wu et al., "In Vitro and In Vivo Study of Phloretin-induced Apoptosis in Human Liver Cancer Cells Involving Inhibition of Type II Glucose Transporter," *Int. J. Cancer*, 124(9), pp. 2210-2219 (May 1, 2009).

Yang et al., "Apple Polyphenol Phloretin Potentiates the Anticancer Actions of Paclitaxel Through Induction of Apoptosis in Human Hep G2 Cells," *Molecular Carcinogenesis*, 48(5), pp. 420-431 (May 2009).

Yung et al., "Microbiological Effect of Photodynamic Therapy (PDT) in Healthy Volunteers: A Comparative Study Using Methyl Aminolaevulinate and Hexyl Aminolaevulinate Cream," *Clinical and Experimental Dermatology*, 32(6), pp. 716-721 (Nov. 2007).

Non-Final Office Action in U.S. Appl. No. 12/798,416 mailed Feb. 6, 2013.

An et al., 0.5% Liposome-encapsulated 5-aminolevulinic acid (ALA) photodynamic therapy for acne treatment, J Cosmet Laser Ther, 28-32, (Feb. 13, 2011).

de Leeuw et al., "Fluorescence Detection and Diagnosis of Non-Melanoma Skin Cancer at an Early Stage," Lasers in Surgery and Medicine, 41(2), pp. 96-103 (Feb. 2009).

Gottschalck et al., "Phloretin", International Cosmetic Ingredient Dictionary and Handbook, vol. 2, pp. 2004.

Klein et al., "Photodynamic Therapy in Dermatology—An Update 2008," Journal of the German Society of Dermatology, 6(10), pp. 839-846 (Oct. 2008).

SkinCeuticals, "Phloretin CF Broad-Range Antioxidant Treatment", Database GNPD Online, www.gnpd.com Jan. 2009.

Yeung et al., Liposome-Encapsulated 0.5% 5-Aminolevulinic Acid with Intense Pulsed Light for the Treatment of Inflammatory Facial Acne: A Pilot Study. Dermatologic Surgery, 37: 241, (Mar. 17, 2011).

European Search Report in Application No. EP10159178 dated Jul. 2, 2015.

\* cited by examiner

 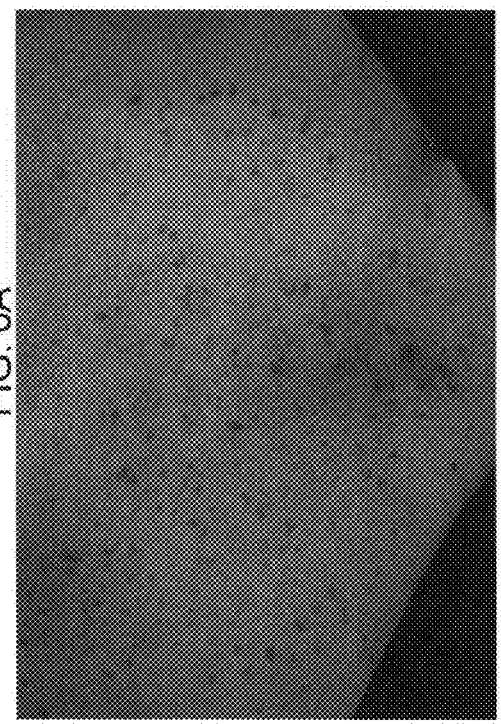
FIG. 6A
FIG. 6B

SYSTEMS AND METHODS FOR SKIN REJUVENATION

RELATED APPLICATIONS

This application is a continuation application of U.S. application Ser. No. 12/798,416, filed Apr. 2, 2010, which claims the benefit of and priority to U.S. Provisional Application Ser. No. 61/166,192, filed Apr. 2, 2009, and to U.S. Provisional Application Ser. No. 61/166,165, filed Apr. 2, 2009, all of which are hereby incorporated herein by reference in their entirety for the teachings therein.

FIELD

The embodiments disclosed herein relate to systems and methods for skin rejuvenation, and more particularly to chemical peels.

BACKGROUND

Chemical peels are among the most frequently performed aesthetic procedures in the United States, and are commonly used for the purpose of rejuvenating the skin. The popularity of chemical peels continues to increase due to the wide range of benefits and conditions for which chemical peels are useful. Broadly speaking, chemical peels can be divided into several categories based on the depth of penetration of the skin. For instance, medium depth peels, peels penetrating the upper reticular dermis, may promote skin smoothness and vitality while improving superficial discoloration and reducing fine wrinkles. Superficial chemical peels, peels penetrating to the basal membrane, may induce skin exfoliation and may lead to a smooth texture, skin brightness and a younger look appearance.

SUMMARY

Systems and methods for skin rejuvenation are disclosed herein.

According to aspects illustrated herein, a system for skin rejuvenation includes a booster product for activating a skin area to be treated; at least one exfoliating product for exfoliating the skin area; and a nano-additive product for enhancing penetration of the booster product and the exfoliating product inside the skin area. In an embodiment, the system is a chemical peel system. In an embodiment, the chemical peel system is a ferulic acid (FA) chemical peel system. In an embodiment, the FA chemical peel system is an antioxidant based peel.

According to aspects illustrated herein, a skin rejuvenation system includes a unit dose of a booster product in a first container for activating a skin area to be treated; a unit dose of at least one exfoliating product in a second container for exfoliating the skin area; and a unit dose of a nano-additive product in a third container for enhancing penetration of the booster product and the exfoliating product inside the skin area. In an embodiment, the skin rejuvenation system is a chemical peel system. In an embodiment, the chemical peel system is a ferulic acid (FA) chemical peel system. In an embodiment, the FA chemical peel system is an antioxidant based peel.

According to aspects illustrated herein, a skin rejuvenation system includes a unit dose of a booster product in a first container for activating a skin area to be treated, the booster product comprising ferulic acid and phloretin in a dermatologically acceptable carrier; a unit dose of at least one exfoliating product in a second container for exfoliating the skin area, the exfoliating product comprising ferulic acid and phloretin in a dermatologically acceptable carrier; and a unit dose of a nano-additive product in a third container for enhancing penetration of the booster product and the exfoliating product inside the skin area, the nano-additive product comprising ferulic acid and phloretin in liposomes. In an embodiment, the skin rejuvenation system is a ferulic acid (FA) chemical peel system. In an embodiment, the FA chemical peel system is an antioxidant based peel.

According to aspects illustrated herein, a skin rejuvenation kit includes a unit dose of a booster product in a first container comprising ferulic acid and phloretin in a mixture of ethanol and macrogol; a unit dose of at least one exfoliating product in a second container comprising ferulic acid and phloretin in a mixture of ethanol and macrogol; and a unit dose of a nano-additive product in a third container comprising ferulic acid and phloretin encapsulated in liposomes. In an embodiment, the nano-additive product further includes at least one of azelaic acid, nicotinic acid, retinol, and ceramides. In an embodiment, a concentration of ferulic acid in the exfoliating product is less than a concentration of ferulic acid in the booster product. In an embodiment, the liposomal lipid is a phosphatidylcholine (PC).

According to aspects illustrated herein, an antioxidant based peel includes a unit dose of an activating product, the activating product including active ingredients of ferulic acid and phloretin in a mixture of ethanol and macrogol; a unit dose of at least one exfoliating product, the exfoliating product including active ingredients of ferulic acid and phloretin in combination with one of fruit acids or alpha hydroxyacids in a mixture of ethanol and macrogol; and a unit dose of an enhancing product, the enhancing product including active ingredients of ferulic acid and phloretin in liposomes.

According to aspects illustrated herein, a method for skin rejuvenation includes applying topically to a skin surface to be treated a booster product for activating the skin; applying topically to the skin surface at least one-exfoliating product for exfoliating the skin; and applying topically to the skin surface a nano-additive product for enhancing penetration of the booster product and the exfoliating product into the skin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 6A is a photograph showing a patient with extensive sun damage of the V of the neck before receiving an embodiment of a Ferulac peel of the present disclosure.

FIG. 6B is a photograph showing improvement in color and reduced sun spotting on the patient shown in FIG. 6A after two application of the Ferulac peel at one week interval in between treatments.

Figure 1:
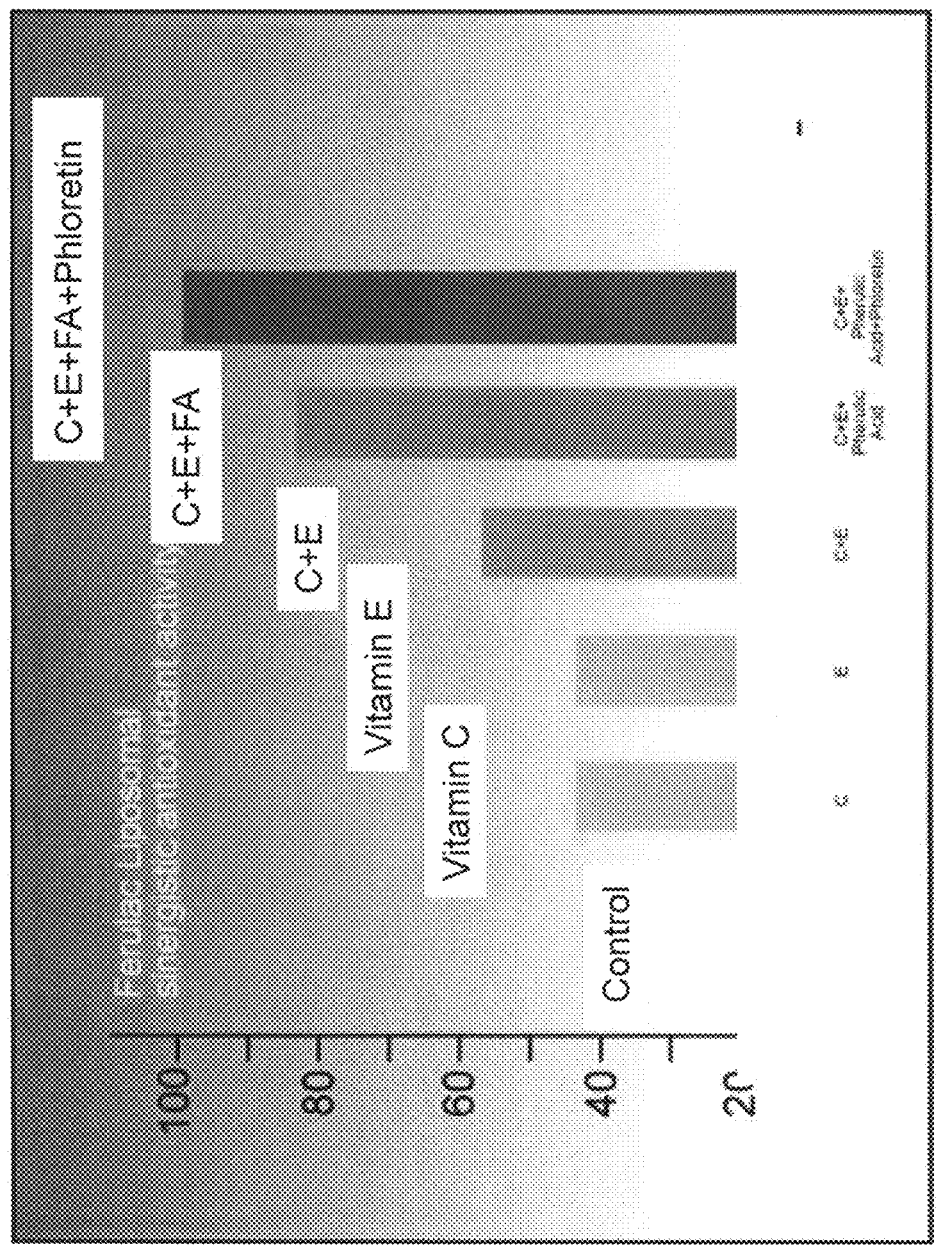
FIG. 1 is a graph showing synergism of various active ingredients used in a Ferulac peel of the present disclosure, and in particular showing Vitamin C, ferulic acid, phloretin and other polyphenolic compounds exhibiting a synergistic effect.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

As used herein, the terms "Ferulac", "Ferulac peel", "FA chemical peel system", "antioxidant peel system", "skin rejuvenation system" and "skin rejuvenation kit" are used to refer to skin rejuvenation treatments of the present disclosure that include, but are not limited to, at least one or more of the following products: Ferulac classic of the present disclosure, Ferulac plus A of the present disclosure, Ferulac plus B of the present disclosure, Ferulac Nano-additive of the present disclosure, an Anti-Acne Nano-additive of the present disclosure, C-Vit of the present disclosure, and OxySeS of the present disclosure. In an embodiment, a product used in a Ferulac peel of the present disclosure is formulated as a cream, an ointment, a solution, a serum, a lacquer spray, a mist spray, a skin stick, a paste, a pledget, a wipe, a cleanser, a gel or suitable combinations thereof. In an embodiment, a product used in a Ferulac peel of the present disclosure is formulated as a chemical solution.

As used herein, the term "dermatologically acceptable carrier" refers to vehicles, diluents, carriers, which can include adjuvants, additives, or excipients, known for use in dermatological compositions. In an embodiment, the dermatologically acceptable carrier is a mixture of ethanol and macrogol. In an embodiment, the ethanol and macrogol mixture may include ethanol and macrogol in a ratio of 2 parts ethanol to 5 parts macrogol.

As used herein, the term "unit dose" is intended to mean an effective amount of substance, or an effective number of articles, adequate for a single session. By way of example, a unit dose of a chemical solution of the present disclosure for the face may be defined as enough solution for a person to coat the face. The surface area of the face may vary somewhat from person to person. Thus, a person using a unit dose may have excess solution left over. It is desirable to provide enough solution that even the above-average sized face will have an effective amount of coverage. In an embodiment, a unit dose of a chemical solution of the present disclosure is contained within a container. In an embodiment, a unit dose of a chemical solution of the present disclosure is contained in an ampoule.

In an embodiment, skin rejuvenation systems, kits and methods are provided for at-home chemical skin peeling. In an embodiment, skin rejuvenation systems, kits and methods are provided for use in dermatologists' or aestheticians' offices. In an embodiment, a skin rejuvenation system of the present disclosure comprises a booster product, an exfoliating product, and a nano-additive product. In an embodiment, a skin rejuvenation system of the present disclosure may be used for superficial depth penetration peeling such as penetration of the stratum corneum all the way down up to the basal membrane. In an embodiment, a skin rejuvenation system of the present disclosure may be used for medium depth penetration peeling so as to reach the upper dermis.

In an embodiment, an antioxidant peel system of the present disclosure comprises a booster product comprising active ingredients in a mixture of ethanol and macrogol, an exfoliating product comprising active ingredients in a mixture of ethanol and macrogol, and a nano-additive product comprising active ingredients encapsulated in unilamellar phosphatidylcholine liposomes. In an embodiment, the active ingredients in the booster product comprises ferulic acid and phloretin. In an embodiment, the active ingredients in the exfoliating product comprises ferulic acid and phloretin. In an embodiment, the active ingredients in the nano-additive product comprises ferulic acid, phloretin, azelaic acid, nicotinic acid, retinol, ceramides, phytosphingosine, zinc and soy bean extract. In an embodiment, the concentration of ferulic acid in the exfoliating product is less than a concentration of ferulic acid in the booster product.

In an embodiment, the booster product comprises the active ingredients ferulic acid and phloretin, in a dermatologically acceptable carrier. In an embodiment, a concentration of the ferulic acid is about 12%. In an embodiment, a concentration of the phloretin is about 5%.

In an embodiment, the exfoliating product comprises the active ingredients ferulic acid, phloretin, a mix of alpha hydroxyacids, and retinol or a retinol derivative in a dermatologically acceptable carrier. In an embodiment, a concentration of the ferulic acid is about 8%. In an embodiment, a concentration of the phloretin is about 5%. In an embodiment, a concentration of the mix of alpha hydroxy acids is about 5%. In an embodiment, a concentration range of the retinol is from about 0.25% to about 0.50%. In an embodiment, a concentration range of the retinol derivative is from about 0.025% to about 0.050%. In an embodiment, the dermatologically acceptable carrier is a mix of ethanol and macrogol.

In an embodiment, the exfoliating product comprises the active ingredients ferulic acid, phloretin, caffeic acid, rosmarinic acid, and trichloroacetic acid in a dermatologically acceptable carrier. In an embodiment, a concentration of the ferulic acid is about 8%. In an embodiment, a concentration of the phloretin is about 5%. In an embodiment, a concentration of the caffeic acid is about 5%. In an embodiment, a concentration of the rosmarinic acid is about 5%. In an embodiment, a concentration of the trichloroacetic acid is about 15%. In an embodiment, a concentration of the trichloroacetic acid is about 20%. In an embodiment, the dermatologically acceptable carrier is a mix of ethanol and macrogol.

In an embodiment, the nano-additive product comprises the active ingredients ferulic acid, phloretin, azelaic acid, nicotinic acid, retinol, ceramides, phytosphingosine, zinc, and isoflavones (from soy bean extract) encapsulated in unilamellar phosphatidylcholine liposomes.

In an embodiment, a method for skin rejuvenation includes topically applying to skin to be treated a booster product, at least one exfoliating product, and a nano-additive product. In an embodiment, the method for skin rejuvenation includes topically applying to skin to be treated two exfoliating products. In an embodiment, the booster product includes about 12% ferulic acid and about 5% phloretin in a dermatologically acceptable carrier. In an embodiment, the exfoliating product includes at least about 8% ferulic acid, about 5% phloretin, an about 5% mix of alpha hydroxy acids (e.g., malic acid, citric acid, and lactic acid), and about 0.25% to about 0.50% retinol or about 0.025% to about 0.050% retinol derivative (e.g., retinaldehyde or tretinoin) in a dermatologically acceptable carrier. In an embodiment, the exfoliating product includes at least about 8% ferulic acid, about 5% phloretin, about 5% caffeic acid, about 5% rosmarinic acid, and about 15% to about 20% tricholoroacetic acid in a dermatologically acceptable carrier. In an embodiment, the dermatologically acceptable carrier is a vehicle comprising a mixture of ethanol and macrogol. In an embodiment, the nano-additive product may be formulated as a solution. In an embodiment, the nano-additive product includes at least ferulic acid, phloretin, azelaic acid, nicotinic acid, retinol, ceramides, phytosphingosine, zinc, and isoflavones (from soy bean extract) encapsulated in unilamellar phosphatidylcholine liposomes.

The use of ferulic acid and phloretin at low strengths (about 0.5% and about 2%, respectively) has been reported for the treatment of several skin conditions and in particular skin photoaging due to the antioxidant action through which ferulic acid and phloretin neutralize free radical damage and protect against oxidative stress. Free radicals and oxidative stress are believed to be the factors that lead to premature aging, loss of elasticity, and hyper-pigmentation associated with chronic sun exposure (i.e., solar lentigines). However, improvement of these conditions, for example, solar lentigines, may take several months. It is believed that the use of higher strengths of ferulic acid and phloretin in chemical peels has been not reported, possibly because it was previously thought that the higher concentrations would be difficult to prepare because the incorporation of ferulic acid into an aqueous phase is problematic and also because phloretin is insoluble in water but very soluble in ethanol. Ferulic acid is not easily incorporated into an oil phase of emulsions or anhydrous compositions, due to ferulic acid's limited solubility in cosmetically acceptable solvents other than water. Ferulic acid is soluble in water at a neutral or alkaline pH (i.e., pH 7 and above). At an acidic pH, ferulic acid precipitates into crystals, is deposited into the crystallized form onto the skin and therefore cannot be delivered to the skin. Similarly, it is believed that the combination of ferulic acid and phloretin with other polyphenols, exfoliating agents (e.g., alpha hydroxy acids "AHA" and trichloroacetic acid "TCA") and retinoids has not been reported. In an embodiment, the present disclosure provides cosmeceutical products having ferulic acid and phloretin at a highest concentration than conventionally used in a chemical peel formulation. In an embodiment, a peel of the present disclosure uses the highest concentrations of ferulic acid and phloretin believed to be safe and effective for periodic application to the skin by using a vehicle comprising a mixture of ethanol and macrogol.

Use of higher concentrations of ferulic acid and phloretin and a low strength synergistic combination of selected active ingredients may provide several advantages: clinical results are more complete and are obtained faster; peel-induced skin irritation is reduced due to the antioxidant; and anti-inflammatory effects of some of the ingredients in the products. The combination of different active ingredients may also provide a mixed action mechanism where TCA may act through a caustic mechanism while ferulic acid, phloretin, azelaic acid, AHAs and retinol may follow a metabolic mechanism. In the case of TCA a toxic effect on keratinocytes and fibroblasts may also exist. Other chemicals such us glycolic acid may not alter the metabolism of fibroblasts but induces the secretion of cytokines (IL-6).

Figure 2:
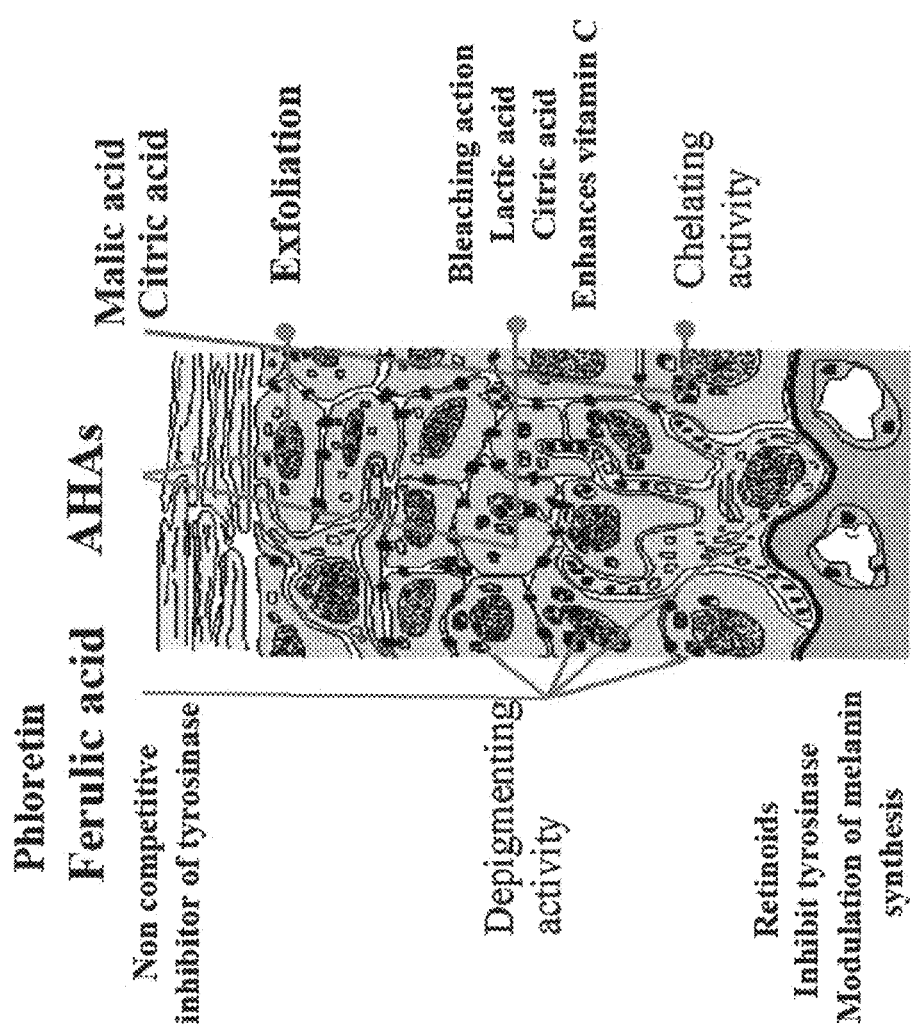
FIG. 2 is a schematic illustration showing the synergistic antioxidant and depigmenting activity of various active ingredients present in an embodiment of a Ferulac peel of the presently disclosed embodiments.

Illustrative of the synergistic effects of the presently disclosed embodiments, FIG. 1 shows a graph of synergistic antioxidant activity of an embodiment of a Ferulac peel of the present disclosure. As shown in FIG. 1, Vitamin C and Vitamin E alone demonstrated more than twice as much antioxidant activity as the vehicle (mixture of ethanol and macrogol) alone used as a control. However, when combined, Vitamin C and Vitamin E can achieve increased antioxidant activity due to a synergistic effect resulting from the combination. As shown in FIG. 1, antioxidant activity is increased substantially when ferulic acid and phloretin and other phenolic compounds are combined with Vitamin C and Vitamin E. The polyphenol derivatives (ferulic acid, phloretin, caffeic acid, rosmarinic acid) show stronger antioxidant activity (more than twice) when they are combined with Vitamin C and Vitamin E (synergism). FIG. 2 is a schematic illustration showing the synergistic antioxidant and depigmenting activity of various active ingredients present in an embodiment of a Ferulac peel of the presently disclosed embodiments. As shown in FIG. 2, the active ingredients can reach the melanocyte and the fibroblast to modulate their activity.

While not wishing to be bound by any one theory, it is believed that the mixture of ethanol and macrogol comprising the vehicle of an antioxidant peel system of the present disclosure evaporates gradually while releasing the active ingredients into the skin until a whitish mask is developed on the skin. That is, the active ingredients are absorbed into the skin as the active ingredients are gradually being released from the vehicle as the vehicle evaporates until a whitish mask forms due to crystallization of the active ingredients. In other words, the crystallization of the active ingredients forms the white mask, i.e., the end point at which the vehicle has substantially evaporated and release of the active ingredients has been substantially neutralized.

In an embodiment, an antioxidant peel system of the present disclosure comprises a gradual release peel. In an embodiment, an antioxidant peel system of the present disclosure provides a gradual release peel due to the vehicle evaporating simultaneously while gradually releasing the active ingredients. In an embodiment, upon application of a coating of a product of an antioxidant peel system of the present disclosure to the skin treatment area, the active ingredients may be gradually released over a period time lasting as long as about 6 minutes. In an embodiment, the gradual release of the peel active ingredients from the vehicle provided by the antioxidant peel system may last for as long as about 6 minutes. In an embodiment, the gradual release peel comprises a slow release peel. In an embodiment, the gradual release peel comprises a prolonged release peel. In an embodiment, the gradual release peel comprises a controlled release peel.

In an embodiment, the gradual release of the peel active ingredients from the vehicle provided by an antioxidant peel system of the present disclosure may last for as long as about 5 minutes. In an embodiment, the gradual release of the peel active ingredients from the vehicle provided by an antioxidant peel system of the present disclosure may last for as long as about 4 minutes. In an embodiment, the gradual release of the peel active ingredients from the vehicle provided by an antioxidant peel system of the present disclosure may last for as long as about 3 minutes.

In an embodiment, an antioxidant peel system of the present disclosure comprises a self-neutralizing peel. In such embodiments, the self neutralizing peel may self-neutralize the peel active ingredients in about 6 minutes. In such embodiments, the self neutralizing peel may self-neutralize the peel active ingredients in about 5 minutes. In such embodiments, the self neutralizing peel may self-neutralize the peel active ingredients in about 4 minutes. In such embodiments, the self neutralizing peel may self-neutralize the peel active ingredients in about 3 minutes.

In an embodiment, an antioxidant peel system of the present disclosure comprises active ingredients that crystallize to form a whitish mask end point to indicate that a coating is substantially complete. In such embodiments, crystallization of the active ingredients may occur within about the first 3 minutes of coating the skin with a product of the antioxidant peel system present disclosure. In such embodiments, crystallization of the active ingredients may occur within about the first 4 minutes of coating the skin with a product of the antioxidant peel system present disclosure. In such embodiments, crystallization of the active ingredients may occur within about the first 5 minutes of coating the skin with a product of the antioxidant peel system present disclosure. In such embodiments, crystallization of the active ingredients may occur within about the first 6 minutes of coating the skin with a product of the antioxidant peel system present disclosure.

In an embodiment, an antioxidant peel system of the present disclosure comprises active ingredients that are absorbed into the skin upon release from the vehicle for a limited period of time. In such embodiments, the active ingredients of a product of the antioxidant peel system present disclosure may be absorbed into the skin for a period of time lasting up to about 6 minutes. In such embodiments, the active ingredients of a product of the antioxidant peel system present disclosure may be absorbed into the skin for a period of time lasting up to about 5 minutes. In such embodiments, the active ingredients of a product of the antioxidant peel system present disclosure may be absorbed into the skin for a period of time lasting up to about 4 minutes. In such embodiments, the active ingredients of a product of the antioxidant peel system present disclosure may be absorbed into the skin for a period of time lasting up to about 3 minutes.

The skin rejuvenation systems and methods of the presently disclosed embodiments are useful in the treatment of skin disorders, particularly those disorders affecting skin surfaces commonly exposed to sunlight, including, but not limited to: photodamaged skin; photoaged skin; hyperpigmentation, including melasma; acne vulgaris, including inflammatory acne, comedonal acne and mild-to-moderate scarring resulting from acne or other atrophic scarring; rosacea; sun spots; freckles; solar lentigenes; premalignant skin cancer; wrinkles; stretch-marks; or superficial scars and other similar common skin problems.

Polyphenolic acids are characterized by the presence of more than one phenol group (e.g., $C_6$—$H_5$—OH). Polyphenolic acids utilized in the present disclosure may include, but are not limited to, ferulic acid, caffeic acid, and rosmarinic acid.

Ferulic Acid

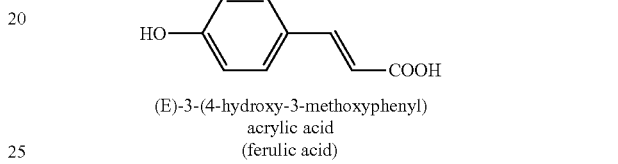

Formula 1

(E)-3-(4-hydroxy-3-methoxyphenyl)
acrylic acid
(ferulic acid)

Ferulic acid (Formula 1) is a phenol derivative, with antioxidant properties and is reactive toward free radicals such as reactive oxygen species (ROS). ROS and free radicals are implicated in DNA damage, cancer, and accelerated cell aging. Animal studies and in vitro studies suggest that ferulic acid may have direct antitumor activity against breast cancer and liver cancer. Ferulic acid may have pro-apoptotic effects in cancer cells, thereby leading to destruction of the cells. Ferulic acid may be effective at preventing cancer induced by exposure to the carcinogenic compounds benzopyrene and 4-nitroquinoline 1-oxide. If added to a topical preparation of ascorbic acid and vitamin E, ferulic acid may reduce oxidative stress and formation of thymine dimers in skin. In addition, it is believed that ferulic acid may protect vitamin A and vitamin C thereby improving the photoprotective action of these vitamins. Ferulic acid may also supplement protection provided by off-the-shelf sunscreens. In combination with vitamin C, ferulic acid may provide two to four times as much photoprotection against ultraviolet radiation thus helping to minimize the harmful effects (e.g., erythema or formation of sun-burn cells) caused by ultraviolet radiation. Ferulic acid may also improve the chemical stability of vitamin C and vitamin E to enhance a synergistic and longer lasting photoprotective effect. While not wishing to be bound to any one theory, it is believed that ferulic acid is a non competitive inhibitor of tyrosinase, an enzyme that catalyses the oxidation of phenols. By inhibiting the effect of tyrosinase, oxidation of the phenolic residues on vitamin C and vitamin E may be reduced resulting in improved chemical stability. Ferulic acid may also confer anti-inflammatory action.

Although ferulic acid per se may be used for the presently disclosed embodiments, a person of ordinary skill in the art will appreciate that derivatives of ferulic acid, e.g., esters, salts and other dermatologically effective derivatives of ferulic acid, may also exhibit similar functionality when used as concentrated solutions in lieu of ferulic acid, and such functional equivalents of ferulic acid are intended to be within the spirit and scope of the presently disclosed embodiments.

Caffeic Acid

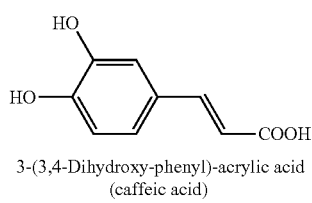

3-(3,4-Dihydroxy-phenyl)-acrylic acid
(caffeic acid)

Caffeic acid (3,4-dihydroxycinnamic acid) (Formula 2) is found in several grains, fruits, and vegetables. Caffeic acid also occurs in coffee, particularly in esterified form, chlorogenic acid (5-caffeoylquinic acid). Caffeic acid is a key constituent of kigelia fruit extract, which has shown significant anticarcinogenic activity and is used in various parts of the world, outside the United States, to defend against skin cancer. Some of the best sources of caffeic acid are white grapes, white wine, olives, olive oil, spinach, cabbage, asparagus, and coffee. Caffeic acid is one of the hydroxycinnamic acids, which are the most widely dispersed class of phenylpropanoids in plants, and which also include ferulic acid and coumaric acid. Like other polyphenolic acids such as ferulic, ellagic, and tannic acid, caffeic acid is thought to have considerable anticarcinogenic potential, and is known to confer antioxidant activity. Caffeic acid may be conjugated with saccharides, can react with nitrogen oxides, and has been shown to protect phospholipidic membranes from UV-induced peroxidation. More significantly, caffeic acid also can protect human skin from UVB-induced erythema due to its antioxidant free radical scavenging activity.

Although caffeic acid per se may be used for the presently disclosed embodiments, a person of ordinary skill in the art will appreciate that derivatives of caffeic acid, e.g., esters, salts and other dermatologically effective derivatives of caffeic acid, may also exhibit similar functionality when used as concentrated solutions in lieu of caffeic acid, and such functional equivalents of caffeic acid are intended to be within the spirit and scope of the presently disclosed embodiments.

Rosmarinic Acid

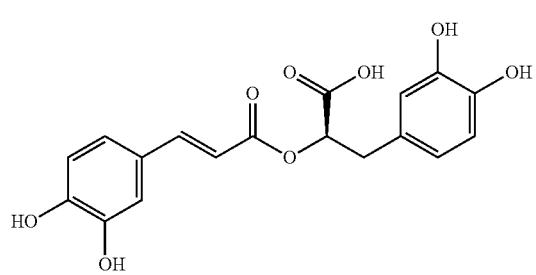

Rosmarinic acid (alpha-o-caffeoyl-3,4-dihydroxyphenyl lactic acid) ("RA") (Formula 3) is a naturally occurring hydroxylated compound and analogue of caffeic acid (3,4-dihydroxycinnamic acid). Caffeic acid and its derivatives, such as rosmarinic acid, carnosol, and carnosic acid—all of which manifest antioxidant activity—are thought to be the key constituents of rosemary. Notably, rosmarinic acid is a common component of some fern and hornwort species, as well as species of the Boraginaceae family and, particularly, the Lamiaceae family. The Lamiaceae family includes common culinary herbs such as basil, lavender, lemon balm, marjoram, oregano, peppermint, perilla, sage, savory, thyme, and rosemary. Rosmarinic acid is well absorbed through the gastrointestinal tract and the skin, and has been shown to augment prostaglandin E2 production and reduce leukotriene B4 production in human polymorphonuclear leukocytes. Rosmarinic acid is versatile, and used in food preservatives, cosmetics, and medical applications because of rosmarinic acid's antimicrobial, antiviral, antioxidant, anti-inflammatory, and immunomodulatory properties. Rosmarinic acid was identified as a nonsteroidal anti-inflammatory agent. Oral supplementation with the polyphenol was an effective treatment for seasonal allergic rhinoconjunctivitis, due to inhibition of the inflammatory response and the scavenging of reactive oxygen species exhibited by the compound. Antitumorigenic effects of a rosmarinic acid are due to free radical scavenging, and inflammatory response suppression. Rosmarinus officinalis extracts shows antimicrobial activity linked to their phenolic composition, (carnosic acid and rosmarinic acid). Rosmarinic acid shows also photoprotective effects against alterations induced by UVA exposure in a human keratinocyte cell lines. The application of a 0.3% rosmarinic acid emulsion on mild atopic dermatitis improves some symptoms of the disease including the erythema, transepidermal water loss, xerosis and pruritus.

Although rosmarinic acid per se may be used for the presently disclosed embodiments, a person of ordinary skill in the art will appreciate that derivatives of rosmarinic acid, e.g., esters, salts and other dermatologically effective derivatives of rosmarinic acid, may also exhibit similar functionality when used as concentrated solutions in lieu of rosmarinic acid, and such functional equivalents of rosmarinic acid are intended to be within the spirit and scope of the presently disclosed embodiments.

Other dermatological acids which may be used in the Ferulac peels of the presently disclosed embodiments include, but are not limited to, glycolic acid, mandelic acid, other AHAS, salicylic acid, trichloroacetic acid, derivatives thereof, and other equivalent dermatological acids having similar properties.

Exfoliation can be beneficial for beautifying and rejuvenating the skin. Frequent exfoliation can help rid the skin of dead tissues, oil, dirt, as well as makeup residues. Exfoliating the skin helps provide glowing skin, and can also minimize or prevent wrinkles and fine lines. Exfoliating agents are believed to act by removing clogged residues from skin pores, and may even prevent acne.

Phloretin

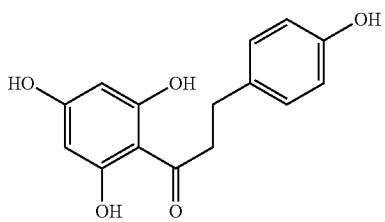

Phloretin (Formula 4) is a flavonoid found exclusively in apples and in apple-derived products where phloretin is present as the glucosidic form, namely, phloridzin (phloretin 2'-O-glucose). Phloretin may protect against free radicals and other reactive molecules known to cause damage and DNA mutations among the integral cell types. Phloretin may also correct existing damage by stimulating the synthesis of essential proteins and fibers and accelerating cell turnover. For example, phloretin may inhibit the formation of MMP-1, an enzyme responsible for breaking down collagen. Another example in which phloretin may correct existing damage is by interrupting melanin synthesis to potentially reduce unwanted skin discolorations. Phloretin is also believed to have immunosuppressor, anti-inflammatory, antifungal, and anti-neoplastic properties which may be useful in accomplishing a synergistic effect in the presently disclosed embodiments. Phloretin may also act as penetration enhancer for the percutaneous delivery of certain topically applied drugs by increasing the fluidity of the intercellular lipid bilayers of the stratum corneum. The interaction of phloretin with stratum corneum lipids would reduce the diffusional resistance of the stratum corneum to drugs with balanced hydrophilic-lipophilic characteristics.

Although phloretin per se may be used for the presently disclosed embodiments, a person of ordinary skill in the art will appreciate that derivatives of phloretin, e.g., dihydrochalcone derivatives, and other dermatologically effective derivatives of phloretin, may also exhibit similar functionality when used as concentrated solutions in lieu of phloretin, and such functional equivalents of phloretin are intended to be within the spirit and scope of the presently disclosed embodiments.

Alpha Hydroxy Acids

Alpha hydroxy acids ("AHAs"), e.g., fruit acids, used in the disclosed embodiments may include at least citric acid, malic acid, and lactic acid. AHAs are well known acids, and are readily available in highly purified form, from a variety of commercial sources, including chemical and laboratory supply houses. Methods for making and extracting AHAs are also well known in the literature. A person of ordinary skill in the art will appreciate that other AHAs, and dermatologically effective derivatives of AHAs, may also exhibit similar functionality when used in concentrated solutions in lieu of citric acid, malic acid, lactic acid, and such functional equivalents of AHAs are intended to be within the spirit and scope of the presently disclosed embodiments.

AHAs are credited with a number of physiological effects on the skin including the break down of intercellular bonds that bind dead skin cells, the removal of accumulated cell debris from the skin surface, the promotion of collagen production, the reduction in age spots, and a moisturizing effect. While not wishing to be bound to any one theory, it is believed that the addition of AHAs (e.g., citric acid and malic acid) in peels containing ferulic acid and phloretin increases the penetration of peel active ingredients, and enhances the synergistic action of ferulic acid and phloretin. The decrease in the thickness of the cornea layer induced by the AHAs and the alteration in the lipid membranes induced by phloretin enhance the epidermal penetration of the actives. Phloretin is a penetration enhancer for percutaneous delivery of certain topically applied drugs. Its mechanism of action is believed to be due to its increase of the fluidity of the intercellular lipid bilayers of the stratum corneum, that is to say, phloretin interacts with stratum corneum lipids to reduce the diffusional resistance of the stratum corneum to drugs and balance the hydrophilic-lipophilic characteristics. In an embodiment, the antioxidant peel system of the present disclosure provides enhanced epidermal penetration of the peel active ingredients by a synergistic effect resulting from AHAs decreasing the thickness of the cornea layer and phloretin altering the lipid membranes. In an embodiment, enhanced penetration of the peel active ingredients caused by the synergistic effects of AHAs and phloretin includes enhancing the concentration of active ingredients absorbed into the epidermis as the active ingredients contact the skin surface. In an embodiment, enhanced penetration of the peel active ingredients caused by the synergistic effects of AHAs and phloretin includes enhancing the velocity in which the active ingredients are absorbed into the epidermis as the active ingredients contact with the skin surface. In an embodiment, enhanced penetration of the peel active ingredients caused by the synergistic effects of AHAs and phloretin includes enhancing the penetration depth of the active ingredients within the epidermis.

Tricholoracetic Acid

Trichloroacetic acid ("TCA") is an analogue of acetic acid in which chlorine atoms replace the hydrogen atoms of the methyl group. TCA can be prepared by reacting chlorine with acetic acid in the presence of a suitable catalyst. TCA is also commercially available in certain concentrations. Trichloroacetic acid can be tailored as either an intermediate or deep peeling agent in concentrations ranging from about 20% to about 50% by increasing or decreasing the concentration. For example, by increasing the concentration of TCA to about 50%, the reticular dermis can be reached. TCA is believed to help smooth fine wrinkles, remove superficial blemishes, and correct skin pigmentation problems. TCA may also be beneficial for darker-skinned patients.

Retinoids

Retinoids are compounds chemically related to vitamin A and generically include a cyclic group having a polyene side chain with a polar end group. Retinoids are believed to enhance cell renewal, increase epidermal thickness, and increase dermal thickness. Retinoids can also activate fibroblasts and collagen synthesis which may decrease the depth of wrinkles. Notably, retinoids are also known to increase exfoliation of skin cells from the epidermis. Suitable retinoids may include retinol, tretinoin, isotretinoin, or the like. Retinol, for example, plays a role in epidermal differentiation and cell renewal. Retinol also dissolves keratinization, resurfaces the skin to provide smoothness, and may activate collagen production to enhance skin quality. Retinol may also confer anti-inflammatory action by blocking chemotactic responses of monocytes and neutrophylles. By reducing the size of sebaceous glands retinol may also decrease sebum secretion which can be helpful in reducing acne.

Ferulac Classic—an Embodiment of a Booster Product of the Present Disclosure

In an embodiment, an antioxidant peel system of the present disclosure includes a booster product "Ferulac classic". Ferulac classic may include one or more of the ingredients in the ranges listed in table 1 below.

TABLE 1

Ferulac Classic Ingredients
BOOSTER PRODUCT OF THE PRESENT DISCLOSURE

| Ingredient | Range |
| --- | --- |
| Alcohol | 30%-90% |
| Polyethylene Glycol | 1%-30% |
| Ferulic Acid | 0.01%-15% |
| Phloretin | 0.1%-15% |

Vehicle: Ethanol and macrogol mixture

In an embodiment, a Ferulac classic product includes about 1%, about 2%, about 3%, about 4%, about 5%, about 6%, about 7%, about 8%, about 9%, about 10%, about 11%, or about 12% ferulic acid and about 1%, about 2%, about 3%, about 4%, or about 5% phloretin in a dermatologically acceptable carrier. In an embodiment, a Ferulac classic product of the present disclosure includes about 12% ferulic acid and about 5% phloretin as active ingredients in a dermatologically acceptable carrier. In an embodiment, Ferulac classic is a booster product which may be used for activating and refreshing a patient's skin. In an embodiment, activation of a patient's skin via application of a booster product of Ferulac classic rejuvenates the patient's skin. In an embodiment, application of a booster product of Ferulac classic to a patient's skin activates the patients skin so as to initiate an antioxidant cascade that results in the scavenging of free radicals or reactive oxygen species. In an embodiment, application of a booster product of Ferulac classic to a patient's skin activates the skin to reduce oxidative stress. In an embodiment, activation of the skin by application of the booster product ameliorates symptoms associated with photoaging of the skin. In an embodiment, applying a coating of the booster product of the present disclosure to a patient's skin activates the patient's skin to initiate an anti-inflammatory cascade. In an embodiment, applying the booster product to a patient's skin activates the skin to stimulate the synthesis of essential proteins. In an embodiment, activation of a patient's skin via the booster product stimulates synthesis of essential fibers. In an embodiment, activation of the patient's skin by applying the booster product accelerates cell turnover. In an embodiment, activation of the patients skin via the booster product of the present disclosure stimulates collagen synthesis. In an embodiment, activating the skin with the booster product results in minimal exfoliation. In an embodiment, Ferulac classic may be formulated with a pH having a range from about 3.2 to about 7.0, from about 3.4 to about 6.5, from about 3.6 to about 6.0, from about 3.8 to about 5.5, or from about 4.0 to about 5.0. In an embodiment, the pH of Ferulac classic 3.5. In an embodiment, the pH of Ferulac classic is 4.0.

In an embodiment, the dermatologically acceptable carrier used in the Ferulac classic is a mixture of ethanol and macrogol. The ethanol and macrogol mixture may include ethanol and macrogol in a ratio of 2 parts ethanol to 5 parts macrogol (Quantity of Ethanol/Quantity of Macrogol). In an embodiment, the ethanol is alcohol denaturalized at 96°. In an embodiment, the macrogol has a molecular weight of 4000. While not wishing to be bound to any one theory, it is believed that a vehicle comprising a mixture of 2 parts ethanol to 5 parts macrogol achieves a relative quick white mask end point for treatment coatings. In an embodiment, a white mask can be achieved within about 3 minutes to about 6 minutes of applying a coating of a Ferulac classic. In an embodiment, the antioxidant peel system uses a vehicle comprising a mixture of ethanol and macrogol to achieve maximum concentrations of ferulic acid and phloretin. In an embodiment, the antioxidant peel system utilizes a vehicle comprising a mixture of ethanol and macrogol to safely and effectively use substantially high concentrations of ferulic acid and phloretin. In an embodiment, the booster product of Ferulac classic uses a vehicle comprising a mixture of ethanol and macrogol to optimize the efficacy and safety of using high concentrations ferulic acid and phloretin. In an embodiment, the vehicle allows ferulic acid to be used safely and effectively in the booster product at concentrations as high as about 12%. In an embodiment, the vehicle allows phloretin to be used safely and effectively in the booster product at concentrations as high as about 5%. In an embodiment, the vehicle comprising a mixture of ethanol and macrogol allows for high concentrations of ferulic acid and phloretin to be incorporated into solution at pH levels that are safe and tolerant for the epidermis.

In an embodiment, a Ferulac classic is fabricated using the following protocol: alcohol is mixed with polyethylene glycol until a homogeneous solution is obtained. Phloretin is added to the solution and the solution is agitated until complete dissolution. Ferulic acid is added with the same agitation until a homogeneous and transparent solution is obtained.

Ferulac Plus a—an Embodiment of an Exfoliating Product of the Present Disclosure In an embodiment, an antioxidant peel system of the present disclosure includes an exfoliating product "Ferulac plus A". Ferulac plus A may include one or more of the ingredients in the ranges listed in Table 2 below.

TABLE 2

Ferulac Plus A Ingredients
EXFOLIATING PRODUCT A OF THE PRESENT DISCLOSURE

| Ingredient | Range |
| --- | --- |
| Alcohol | 30%-90% |
| Polyethylene Glycol | 1%-30% |
| Ferulic Acid | 0.01%-15% |
| Phloretin | 0.1%-15% |
| Citric Acid | 0.01%-10% |
| Malic Acid | 0.01%-10% |
| Lactic Acid | 0.01%-10% |
| Retinol | 0.01%-1% |
| Retinaldehyde | 0.01%-1% |
| Tretinoin | 0.01%-1% |

Vehicle: Ethanol and macrogol mixture

In an embodiment, the Ferulac plus A product includes at least 8% ferulic acid, 5% phloretin, a 5% mixture of alpha hydroxyacids, and 0.25% to 0.50% retinol as active ingredients in a dermatologically acceptable carrier. In an embodiment, the dermatologically acceptable carrier used in Ferulac plus A comprises a mixture of ethanol and macrogol as described above for the booster product. In an embodiment, the dermatologically acceptable carrier used in Ferulac plus A comprises a vehicle comprising a mixture of ethanol and macrogol. In an embodiment, Ferulac plus A vehicle comprises a mixture of ethanol and magrogol in a ratio of 2 to 5. In an embodiment, the ethanol is alcohol denaturalized at 96°. In an embodiment, the macrogol has a molecular weight of 4000. In an embodiment, Ferulac plus A may be used as an exfoliant. In an embodiment, Ferulac plus A may be formulated with a pH having a range from about 3.2 to about 7.0, from about 3.4 to about 6.5, from about 3.6 to about 6.0, from about 3.8 to about 5.5, or from about 4.0 to about 5.0. In an embodiment, the pH of Ferulac plus A 3.5. In an embodiment, the pH of Ferulac plus A is 4.0.

In an embodiment, Ferulac plus A is fabricated using the following protocol: alcohol is mixed with polyethylene glycol and lactic acid until a homogeneous solution is obtained. Ferulic acid is slowly added to the solution and mixed with agitation until complete dissolution. Tretinoin, phloretin, citric acid, malic acid, retinol, and retinaldehyde may be added, as desired, and mixed until a homogeneous and transparent solution is obtained.

Ferulac Plus B—an Embodiment of an Exfoliating Product of the Present Disclosure In an embodiment, an antioxidant peel system of the present disclosure includes an exfoliating product "Ferulac plus B". Ferulac plus B includes one or more of the ingredients in the ranges listed in Table 3 below.

TABLE 3

Ferulac Plus B Ingredients
EXFOLIATING PRODUCT OF THE PRESENT DISCLOSURE

| Ingredient | Range |
| --- | --- |
| Alcohol | 30%-90% |
| Polyethylene Glycol | 1%-30% |
| Ferulic Acid | 0.01%-15% |
| Phloretin | 0.1%-15% |
| Caffeic Acid | 0.1%-10% |
| Rosmarinic Acid | 0.1%-10% |
| Lactic Acid | 0.01%-10% |
| Trichoroacetic Acid | 0.1%-30% |

Vehicle: Ethanol and macrogol mixture

In an embodiment, Ferulac plus B includes at least 8% ferulic acid, 5% phloretin, 5% caffeic acid, 5% rosmarinic acid, 5% lactic acid, and 15% trichloroacetic acid as active ingredients in a dermatologically acceptable carrier. In another embodiment, Ferulac plus B may include as much as 20% trichloroacetic acid. In an embodiment, the dermatologically acceptable carrier used in Ferulac plus B comprises a mixture of ethanol and macrogol. In an embodiment, the dermatologically acceptable carrier used in Ferulac plus B comprises a vehicle comprising a mixture of ethanol and macrogol as described above for the booster product. In an embodiment, Ferulac plus B vehicle comprises a mixture of ethanol and magrogol in a ratio of 2 to 5. In an embodiment, the ethanol is alcohol denaturalized at 96°. In an embodiment, the macrogol has a molecular weight of 4000. While not wishing to be bound to any one theory, it is believed that a vehicle comprising a mixture of 2 parts ethanol to 5 parts macrogol achieves a relative quick white mask end point for treatment coatings. In an embodiment, Ferulac plus B may be used as an exfoliant. In an embodiment, Ferulac plus B may be formulated with a pH having a range from about 3.2 to about 7.0, from about 3.4 to about 6.5, from about 3.6 to about 6.0, from about 3.8 to about 5.5, or from about 4.0 to about 5.0. In an embodiment, the pH of Ferulac plus B is 3.5. In an embodiment, the pH of Ferulac plus B is 4.0.

In an embodiment, Ferulac plus B is fabricated using the following protocol: alcohol is mixed with polyethylene glycol and lactic acid until a homogeneous solution is obtained. Ferulic acid is slowly added to the solution and mixed with agitation until complete dissolution. Phloretin, caffeic acid, rosmarinic acid and trichloroacetic acid may be added and mixed until a homogeneous and transparent solution is obtained.

In an embodiment, an antioxidant peel system of the present disclosure includes at least one nano-additive product comprising active ingredients encapsulated in liposomes to increase the peel's beneficial skin effects. In an embodiment, the liposomes are unilamellar. Nano-additive products can be used before, during, or after an extensive list of cosmetic and medical procedures. Nano-additive products are added to the procedure to improve or accentuate beneficial effects and also to minimize side effects. In an embodiment, a nano-additive product of the present disclosure will penetrate the skin due to the nanometer size (100-150 nm). The active ingredients in a nano-additive product of the present disclosure is incorporated into the liposome core or membrane in minute amounts or strengths but equivalent to those strengths frequently used in non-liposomal products. In an embodiment, a nano-additive product of the present disclosure will get relatively high concentrations in the tissues and will not modify the characteristics of the procedure (for example, peel, PDT, Electroporation) or the chemical used for the product.

Anti-Acne Nano-Additive Product

In an embodiment, an antioxidant peel system of the present disclosure includes an "Anti-Acne Nano-additive" product for treating acne. The Anti-Acne Nano-additive product comprises one or more of the ingredients in the specified ranges listed in Table 4 below.

TABLE 4

Anti-Acne Nano-additive Product

| Ingredient | Range |
| --- | --- |
| Bidistillate Water | 30-90% |
| Alcohol | 0.1-40% |
| Lecithin | 0.1-30% |
| Osmose | 0.01-5% |
| Sodium Colate | 0.01-15% |
| Phenoxyethanol | 0.1-1% |
| Citric Acid | 0.01-5% |
| Sodium Lauroyl Lactylate | 0.01-5% |
| Methylsilanol Hydroxiproline Aspartate | 0.01-5% |
| Salicylic Acid | 0.01-15% |
| Polysorbate 20 | 0.1-10% |
| Ascorbyl Methylsilanol Pectinate | 0.01-5% |
| *Glycine Soja* (Soybean) Extract | 0.01-10% |
| Ceramide 3 | 0.001-5% |
| Nordihydroguaiaretic Acid | 0.001-5% |
| Linoleic Acid | 0.001-5% |
| Ceramide 6II | 0.001-5% |
| Phytosphingosine | 0.0001-1% |
| Chlolesterol | 0.001-5% |
| Oleic Acid | 0.001-5% |
| Xantan Gum | 0.001-10% |
| Carbomer | 0.001-10% |
| Lactoferrin | 0.001-2% |
| Lactoperosidase | 0.001-2% |
| Zinc Chloride | 0.0001-1% |
| Linolenic Acid | 0.00001-1% |
| Ceramide 1 | 0.00001-1% |

In an embodiment, the Anti-Acne nano-additive product of the present disclosure can be used during a cosmetic procedure such as acne treatment, treatment of seborrhoea and acne, and treatment of oily skin.

Table 5 below lists the functions of various active ingredients that may be included in the Anti-Acne nano-additive product of the present disclosure.

TABLE 5

Functions of the Anti-Acne Nano-additive Product Ingredients

| Ingredient | Function |
| --- | --- |
| Citric acid | Bactericidal; DHT control |
| Linolenic/linoleic | Replaces EFAs. DHT control |
| Silanols | Healing, inhibit melanogenesis, antioxidant |
| Lactoferrin-Lactoperoxidase | Antibacterial, immuno enhacer, antioxidant |
| Salicylic acid Pyruvic acid | Keratolytic, sebostatic, exfoliant |
| Oleanolic acid | Inhibit 5 alpha reductase Diminish seborrhea |
| Nordihydroguairetic acid | Reduces hyperkeratinization; anti-inflammatory |
| Osmose | Deprives bacteria of water |
| ZIinc | Decrease DHT, control bacteria, enhance healing |
| Ceramides 1, 2, 3, 6-II | Skin barrier |

Ferulac Nano-Additive Product

In an embodiment, an antioxidant peel system of the present disclosure includes a "Ferulac Nano-additive" product. Ferulac Nano-additive product comprises one or more of the ingredients in the specified ranges listed in Table 6 below.

TABLE 6

Ferulac Nano-additive Product Ingredient Ranges

| Ingredient | Range |
|---|---|
| Bidistillate Water | 30-90% |
| Alcohol | 0.1-40% |
| Lecithin | 0.1-30% |
| Sodium Colate | 0.01-15% |
| Phenoxyethanol | 0.1-1% |
| Sodium Lauroyl Lactylate | 0.01-5% |
| Pherulic Acid | 0.001-5% |
| Nicotinic Acid | 0.001-5% |
| Retinol | 0.001-5% |
| Azelaic Acid | 0.01-15% |
| Ceramide 3 | 0.001-5% |
| Phloretin | 0.001-5% |
| Ceramide 6II | 0.001-5% |
| Phytosphingosine | 0.0001-1% |
| Chloresterol | 0.001-5% |
| Xantan Gum | 0.01-15% |
| Carbomer | 0.01-15% |
| Zinc Chloride | 0.001-0.5% |
| Ceramide 1 | 0.001-5% |
| *Glycine Soja* (Soybean) Extract | 0.1-10% |

In an embodiment, the Ferulac nano-additive product of the present disclosure can be used during a cosmetic procedure such as photo aging, skin rejuvenation, acne treatment, freckle removal and treatment, sun spot removal, skin bleaching, and hyperpigmentation removal.

Table 7 below lists the functions of various active ingredients that may be included in the Ferulac nano-additive composition of the present disclosure.

TABLE 7

Functions of the Ferulac Nano-additive Product Ingredients

| Ingredient | Function |
|---|---|
| Zinc | Decrease DHT, control bacteria, enhance healing |
| Ferulic acid | Antioxidant. Stop release of inflammatory FA; quenching free radicals |
| Phloretin | Antioxidant; penetration enhancer |
| Nicotinic acid (B3) | Maintains skin barrier, stimulates collagen, increases food supply to skin by increasing vascularity |
| Azelaic acid | Inhibit 5 alpha reductase; inhibit melanogenesis |
| Retinol | Epithelial differentiation (binding vitamin A to nuclear receptors (RAR, RXR). Cell turn over & keratinization Reduces size and secretion of sebaceous glands. Reduces inflammation by blocking chemotactic responses of monocytes and neutrophils. Remodelling of sebaceous glands |
| Ceramides 1, 2, 3 & 6-II | Skin barrier |

In an embodiment, the Ferulac nano-additive product may act as a penetration enhancer. In an embodiment, the Ferulac nano-additive product includes ceramides 1, 2, 3, & 6-II to improve the barrier function of the skin thereby regulating epidermal water loss, and allowing the skin to more efficiently regulate and repair. In an embodiment, Zinc is included in the Ferulac nano-additive product to decrease dihydrotestosterone ("DHT"), control bacteria, and enhance post-peel healing. Nicotinamide is believed to improve the barrier function of the skin, stimulate collagen production, and increase blood flow and nutrients to the skin cells. Azelaic acid may be provided to inhibit 5-alpha-reductase, as well as to inhibit melanogenesis.

OxySeS

OxySeS is a mist (spray) provided comprising 100% oxygen saturated liposomes, and 10 mg/ml of fructose 1, 6 bisphosphate encapsulated in unilamellar liposomes. In an embodiment, OxySes is referred to as an "oxygen product" of the present disclosure. In an embodiment, the OxySeS mist includes one or more of the following ingredients: water, lecithin, alcohol denat (denaturated alcohol), fructose, tocopherol, sodium chloride, sodium hydroxide, sodium cholate, and phenoxyethanol. OxySeS increases the oxygen content of the skin by delivering $O_2$ through unilamelar liposomes. It is believed that the fibroblast cell activity, responsible for manufacturing collagen and elastin, is dependent on the availability of $O_2$. Fructose 1, 6 bisphosphate is provided for anti-inflammatory and antiradicalar action. Fructose 1, 6 bisphosphate also may promote skin repair and may be useful for conditions associated with poor blood supply or tissular injury. In an embodiment, a main component of the liposomes is phosphatidylcholine. Phosphatidylcholine may be provided: for repairing the stratum corneum to improve the barrier function of skin; for anti-inflammatory action to reduce edema in the treatment area; and for bactericidal activity to avoid proliferation of post-treatment infection.

In an embodiment, OxySeS is applied to the skin to supply additional oxygen to skin tissue before applying a booster product of the present disclosure. For example, once the skin has been cleansed and just prior to application of a Ferulac peel of the present disclosure, OxySeS may be applied. In an embodiment, prior to applying a booster product of the present disclosure, it may be beneficial to apply OxySeS to the areas of skin to be peeled on as many as fifteen or twenty days prior to treatment for optimal preparation and results. In an embodiment, applying OxySeS to the skin to supply additional oxygen to skin tissue after a cosmetic procedure (e.g., a chemical peel) may regenerate and repair the skin. For example, after the last exfoliating product of the present disclosure has been applied according to a treatment protocol disclosed, OxySeS may be applied for post-peel skin healing.

OxySeS may be effective in cases in which an increase of tissue oxygenation is desired, such as photodynamic therapy. Indications for OxySeS therefore may include plastic surgery, phlebology, diabetes, dermatology, and radiotherapy. OxySeS may be indicated for use in plastic surgery following phenol or TCA peels, skin grafts, and for speeding healing processes. In the area of phlebology, OxySeS may be useful for treating venous ulcers and skin necrosis related to sclerotherapy. In the care of diabetes, OxySeS may help diabetics prevent keloid formation. OxySeS may also ameliorate various skin conditions associated with diabetes, such as diabetic feet, diabetic ulcers, and may improve skin elasticity. Dermatological uses of OxySeS can include improving skin elasticity, use before, during, or after aesthetic surgery, pre-peel treatment or post-peel treatment, microdermabrasion, or generally for conditions caused by poor blood supply, smoking, or anaerobic skin infections. Radiotherapy application of OxySeS may include radiodermitis treatment, skin necrosis, or the like.

In those instances where a patient to be treated has impaired circulation, OxySeS may be applied on the area to be treated. Application twice a day for up to as much as about four weeks before the procedure may be advisable. However, less frequent daily application as early as a day before the procedure may also be helpful.

Post procedure use of OxySeS may include application of OxySeS twice daily to the treated area by gentle rubbing. In an embodiment, post procedure use of OxySeS may include applying OxySeS twice daily for a period of up to about four weeks.

C-Vit

Photo-aging results from excessive exposure to Ultra-violate (UV) rays, stress, pollution, and time, which generate an excess of free radicals that the human body is unable to fully neutralize. These free radicals travel through the body and cause damage by attacking stable cells, and oxidizing vital elements like DNA, lipid membranes and structural proteins such as collagen and elastin. This may lead to dehydration, and visible symptoms such as wrinkling of the skin, sun spots, skin roughness, and yellowish skin color.

In an embodiment, a product useful for ameliorating symptoms associated with photoaging is known as "C-Vit", and includes 2% ascorbic acid, vitamin A, vitamin E, and orange extract encapsulated in nanosomes. C-Vit includes liposomal vitamin C serum providing a stable vitamin C protected from the environment due to encapsulation in the nanosome. Encapsulation in nanosomes allows deeper penetration and a gradual release, rendering more effectiveness for the prevention and treatment of facial photo-aging.

In an embodiment, C-Vit provides a tiered effect including an immediate effect and a lasting effect. C-Vit may provide immediate smoothness and luminosity to the skin (e.g., glossing wrinkles). The lasting effect provided by C-Vit includes correcting and reducing symptoms associated with photo-aging of the skin such as dehydration, wrinkles, loss of firmness, and sun spots, for example.

The Vitamin C included in C-Vit is believed to confer antioxidant action, anti-wrinkle action, and depigmenting action. Vitamin C, in the liquid phase, provides an antioxidant action by neutralizing free radicals and inhibiting the skin inflammation caused thereby. Vitamin C acts to stimulate collagen synthesis in fibroblasts which may allow lesions and scars to repair, including wrinkles. Vitamin C also may inhibit synthesis of melanin in the melanocytes while reducing existing melanin to prevent unwanted skin pigmentations.

In an embodiment, C-Vit includes proteoglycans. Proteoglycans may immediately improve the smoothness, elasticity and hydration of the skin. Proteoglycans also may restore connective tissue, allowing the tissue to recover strength and elasticity.

In an embodiment, C-Vit includes Vitamins A and E and Orange extract to reinforce the antioxidant activity (e.g., lipidic phase).

In an embodiment, C-Vit includes phosphatidylcholine, a main component of liposomes, and may improve the function of the skin as a barrier, an anti-inflammatory, a bactericidal, and a sebum regulator. It is believed that phosphatidylcholine may repair the stratum corneum thereby improving the barrier function of skin. Phosphatidylcholine is also believed to provide an anti-inflammatory effect by reducing the edema in the skin area treated. Phosphatidylcholine provides a bactericidal function to help prevent infection proliferation, in part, by improving the barrier function of the skin. As a sebum regulator, phosphatidylcholine may normalize lipids on the cutaeneous surface, increasing linoleic acid levels and decreasing squalene, consequently reducing comedones.

In an embodiment, C-Vit may prevent facial aging associated with various oxidation processes, such as UV exposure, chronological aging, stress, and pollution, to name a few. In some instances, C-Vit may treat the symptoms produced by these oxidation processes, for instance, dehydration, wrinkles, loss of elasticity, and skin pigmentation, or other symptoms associated with oxidation. In an embodiment, C-Vit may also help fight periodontal disease.

In an embodiment, C-Vit may be formulated as a 15 ml mist spray. In another embodiment, C-Vit may be formulated as 2 ml ampoules. In another embodiment, C-Vit may include one or more of the following ingredients water, soluble proteoglycan, lecithin, alcohol denat, ascorbic acid, citrus aurantium dulcis (orange) fruit extract, sodium chloride, retinyl palmitate, tocopherol, sodium hydroxide, sodium cholate, and phenoxyethanol.

In an embodiment, C-Vit may be applied daily on the face and other areas to be treated (e.g., neck, neckline) that have been cleansed prior to a treatment. In an embodiment, once C-Vit has been applied to the areas to be treated, fingertips may be used to massage the areas to be treated until the C-Vit solution has been completely absorbed. In an embodiment, optimum effect may be achieved by focusing massaging on the most affected areas of the skin to be treated.

In the present disclosure, concentrations of ferulic acid between about 10% to about 15% and phloretin between about 3% to about 10% have been formulated and tested (chemically and clinically). It is believed that the use of active ingredients such as ferulic acid and phloretin in a vehicle comprising a mixture of ethanol and macrogol can have a wide range of indications for common skin problems, including, but not limited to acne, rosacea, photo-aging, melasma, sun spots, freckles, atrophic scars, including acne scars, and stretch marks.

In an embodiment, an antioxidant peel system of the present disclosure can be applied to all skin types. In an embodiment, ingredients of the peel system are not deep dermal wounding agents, since the ingredients do not induce any inflammation, pigmentary (e.g., hyperpigmentation) changes are absent. Instead, an improvement of the pigmented lesions (freckles, sun spots, melasma) is observed from the first applications. Improvement of the surface roughness and texture occurs immediately and are frequently seen in mild to moderate photoaging in Fitzpatrick I-IV patients.

In an embodiment, an antioxidant peel system of the present disclosure is applied at intervals of 7 to 14 days for optimal results. In this embodiment, between four and ten total peel treatments are recommended.

Some of the advantages afforded to the antioxidant peel systems of the present disclosure include, but are not limited to: the peels may be used in all skin types, including dark and sensitive skin; the peels have a high safety margin, especially when the peels are applied to intact skin; the peels may be used in patients using retinoids topically or orally; the peels do not require neutralization; and the peels may be combined with other superficial and medium depth peels.

In some embodiments, other conventional chemical peels may be used in combination with, and between peels of the present disclosure. These conventional peels include, but are not limited to, glycolic acid peels, lactic acid, Jett peels, salicylic acid peels, Jessner peels, mandelic acid peels, or other similar peels. In an embodiment, the conventional peel is applied first followed by application of several coats of a peel of the present disclosure. This can allow for a slightly deeper peel.

In an embodiment, peels of the present disclosure may be applied on the face, neck, neckline, hands, arms, or other skin surface to be treated. In an embodiment, peels may be applied to skin surfaces that are frequently exposed to sunlight or other similar forms of radiation that might contain UVR.

Some of the clinical effects afforded to the peels of the present disclosure include, but are not limited to: an improvement of skin color; an improvement of surface roughness; and ideal peel for post inflammatory hyperpigmentation, provided the pigmentation is superficial and not sequestered in dermal melanophages.

In an embodiment, an indication for using a peel of the present disclosure is acne, both comedonal, and papular and pustular acne. Ferulic acid and phloretin are very strong antioxidants and prevents lipid peroxidation of sebum and the inflammatory cascade. In addition, citric, lactic and malic acid acts on acne lesions, and loosen up impacted comedones. Most of the patients with acne treated with a Ferulac peel of the present disclosure showed a reduced sebum secretion after 2 to 3 treatments. It is believed that superficial melasma can also improve with repeated Ferulac peels of the present disclosure, since the peels accelerate epidermal turn over and decrease the amount of reduced melanin.

In an embodiment, a peel of the present disclosure may be beneficial to treat photoaged skin since the peels are believed to increase epidermal and dermal thickness, regulate keratinocyte differentiation, modulate melanocyte activity and increase the synthesis of collagen and glycosamonoglycans.

In an embodiment, patients applying tretinoin or taking retinoids by mouth may consider reducing the number of Ferulac plus coats to two and increasing the application intervals up to every 5-30 days. In an embodiment, the Ferulac peel of the present disclosure does not exfoliate or desquamate the skin. Preparation of the skin with keratolytics (salicylic acid, glycolic acid, and tretinoin) may enhance epidermal penetration of the active ingredients but the products are gentle that there is no contraindication for the application.

In an embodiment, a method for facial skin rejuvenation using an antioxidant peel of the present disclosure includes washing the face with regular soap and abundant water; degreasing the skin with isopropyl alcohol (for example, with a cotton gauze pads); applying a coat of the booster product of the present disclosure to the face (for example, using a gloved hand); and massaging the face for about 2-3 minutes. In an embodiment, application of the booster product of the present disclosure starts over the forehead, then to the cheeks, progressing to the chin, upper lip, nose, and eyelids. In an embodiment, approximately 2 ml to approximately 3 ml of the booster product is used to cover the face, and this can be accomplished in approximately 60 seconds.

Care should be taken not to drip or spray the agent into the eyes or wick it into the conjunctiva. In an embodiment, a small hand-held fan can be used when applying an antioxidant peel to a patient, since some patients may get uncomfortable because of an ethanol smell and may start coughing. The fan does not cause rapid volatilization of the ethanol and macrogol vehicle as in salicylic acid peels because of the macrogol content.

Figure 3B:
FIG. 3B is a photograph showing a white mask end point formed after evaporation of the ethanol on the patient shown in FIG. 3A after proper application of two coats of Ferulac peel of the present disclosure.
Figure 3A:
FIG. 3A is a photograph showing a patient before receiving a coating of an embodiment of a Ferulac peel of the present disclosure. The Ferulac peel includes ferulic acid and phloretin in a mixture of ethanol and macrogol.

In an embodiment, after about 3 minutes to about 6 minutes has elapsed, a white mask develops on the sites of application. In an embodiment, additional booster product coats and/or exfoliating product coats may be applied. In an embodiment, 2 to 4 coats are applied. In an embodiment, a mist of vitamin C encapsulated in liposomes (C-Vit) is applied between coats. In an embodiment, C-Vit mist may be applied subsequent to washing the face but before the first application of the booster solution. FIG. 3A is a photograph showing a patient before receiving a coating of a Ferulac peel solution of the present disclosure. FIG. 3B is a photograph showing a white mask; the ethanolic vehicle volatilizes meaning partial crystallization of the actives. The white mask allows visualization of the application and may help seal the skin with a retinol or retinoid preparation if obtaining stronger action is desired. In an embodiment, because Ferulac plus B includes TCA, a real focal or spotty white frost may appear on the application sites after the application of more than two coats of Ferulac plus B. This is the end point for the peel and no confluent frosting is desired.

In an embodiment, a peel of the present disclosure may be washed for cosmetic purposes. In an embodiment, instead of washing the peel after the last coat of Ferulac peel has been applied, a peel nano-additive composition may be applied to enhance penetration of the peel active ingredients and to enhance healing. However, in the event a patient wants to remove a chemical peel solution, the face can be wiped using cotton gauze pads saturated with water, or more conveniently, the patient can wash his/her face with cold water in the sink.

In an embodiment, an antioxidant peel system of the present disclosure includes a sealant to enhance peel adhesion and for regenerative exfoliating action. The sealant may be applied subsequent to the step of applying the nano-additive composition. In an embodiment, the sealant includes Retises 1% nanopeel gel. In an embodiment, the sealant includes 1% retinol plus hylauronic acid encapsulated in liposomes.

In an embodiment, an antioxidant peel system of the present disclosure includes a protectant to protect the treated skin from subsequent exposure to ultraviolet radiation or other situations associated with photo-damaging of the skin. The protectant may be applied subsequent to the step of applying the nano-additive composition. In an embodiment, the protectant includes sunscreen. In an embodiment, the sun screen may have an SPF ranging from about SPF 10, about SPF 20, about SPF 25, about SPF 30, about SPF 35, about SPF 40, about SPF 45, about SPF 50. In an embodiment, the protectant is formulated as a spray. In an embodiment, the protectant is formulated as a lotion. In an embodiment, the sun screen is formulated as a tinted cream. In an embodiment, the protectant includes a SunySeS brand sun screen. The SunySeS brand sun screen may include one of SunySeS 30 spray, Sunyses 30 lotion, Sunyses 50 tinted cream.

Figure 4B:
FIG. 4B is a photograph showing the effects on the patient shown in FIG. 4A after receiving the Ferulac peel, including improvements of the patient's skin texture (roughness), color (brighter look), and a decrease in the pore size.
Figure 4A:
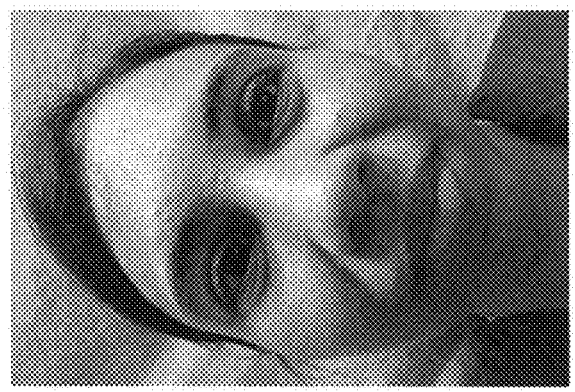
FIG. 4A is a photograph showing a patient before receiving an embodiment of a Ferulac peel of the present disclosure.

FIG. 4A is a photograph showing a patient before receiving a Ferulac peel treatment of the present disclosure. FIG. 4B illustrates the immediate effects noticeable upon completion of a peel of the present disclosure on the patient shown in FIG. 4A. As shown in FIG. 4B, the improvement of the patient's skin texture (roughness), color (brighter look), and a decrease in the pore size is apparent. Long-term use of Ferulac peels may improve skin texture, improve tone, and skin complexion may take on a healthy, vibrant glow. Extended use of Ferulac peels may also reduce fine lines, wrinkles, hyperpigmentation, and age spots.

In some embodiments, an antioxidant peel system of the present disclosure may be used in conjunction or combination with other dermatological treatments or cosmetic procedures to synergistically improve the effects of both the peel and the cosmetic procedures.

In some embodiments, an antioxidant peel system of the present disclosure can be used in conjunction or combination with another skin rejuvenation treatment, including, but not limited to, dermabrasion, microdermabrasion, laser and light resurfacing lasers, IPL and LEDs, plasma technology, radiofrequency technologies, and photodynamic therapy.

Intense Pulsed Light

Intense Pulsed Light (IPL) is a popular cosmetic procedure for rejuvenating skin and removing hair. IPL delivers hundreds of wavelengths in each burst of light. IPL light pulses are usually short in duration to minimize discomfort and damage to non-target tissue. IPL is a common cosmetic procedure that may be carried out by well known protocols.

In an embodiment, a Ferulac peel of the present disclosure may be used in conjunction or in combination with Intense Pulsed Light therapy (IPL). In an embodiment, a Ferulac peel of the present disclosure may be applied prior to an IPL treatment. Using a Ferulac peel prior to IPL treatment may reduce lipidic peroxidation and skin dehydration. Pre-IPL Ferulac peel application may also decrease undesirable inflammation and reduce oxidative stress associated with IPL treatment. Ferulac peeling before IPL treatment may even enhance the effects of the IPL treatment by improving skin texture and decreasing pore sizes. In another embodiment, a Ferulac peel of the present disclosure may be applied after an IPL treatment to enhance healing of target tissue. It is believed that Ferulac peeling post-IPL treatment can be beneficial by promoting antioxidants and collagen production to enhance the healing process, such as speeding up post-IPL treatment hearing.

LEDs

Light Emitting Diodes (LEDs) are used to stimulate cells to produce new collagen and elastin to rejuvenate skin by decreasing wrinkles, age spots, and other similar skin problems associated with collagen and elastin abnormalities. Therapy using LEDs may be carried out by well known protocols. In an embodiment, a Ferulac peel of the present disclosure may be used in conjunction or in combination with LEDs. In an embodiment, a Ferulac peel of the present disclosure may be applied prior to a treatment with LEDs. In an embodiment, a Ferulace peel of the present disclosure may be applied prior to a 525 nm green light LED treatment to reduce hyperpigmentations, freckles, sun spots, and to regulate melanocytes for a brighter complexion. In an embodiment, a Ferulac peel of the present disclosure may be applied prior to a 590 nm yellow light LED treatment as a collagen booster to reduce wrinkles. Wrinkles may also be decreased by boosting collagen levels, in yet another embodiment, by applying a Ferulac peel of the present disclosure prior to 630 nm yellow light LEDs treatment.

In an embodiment, C-Vit may be used in combination with a Ferulac peel of the present disclosure and LEDs to decrease pore sizes and reduce the depth of wrinkles to give the treated individual a vibrant complexion. In this embodiment, a Ferulac peel of the present disclosure can be applied every fourteen days, along with daily application of C-Vit, and LED exposure every seven to fourteen days. C-Vit may be applied once daily for good results, or twice daily for improved results. Combination treatment with C-Vit, a Ferulac peel of the present disclosure and LEDs may improve skin brightness in the first four to seven days. Pore improvement may be noticeable within seven to fourteen days. Longer term treatment, such as over a course of about 30 days, may reduce wrinkles. LED exposure time may vary from anywhere between 10 to 20 minutes depending on the intensity of the LED used. For example, a relatively high intensity lamp may be used for a shorter interval e.g., 10 minutes, whereas a relatively lower intensity lamp may be used for a duration as long as 20 minutes. For optimal results, as many as eight to ten peels can be used in combination with C-Vit and LEDs. It is also believed that combination treatment using C-Vit, a Ferulac peel of the present disclosure, and LEDs may be indicated for active acne, seborrheic dermatitis, and rosacea.

Radiofrequency

Radiofrequency is believed to tighten, remodel, and rejuvenate age-related skin effects by locally contracting collagen fibers. Radiofrequency has also been used to treat acne, and stretch marks, among others. Radiofrequency is a common cosmetic procedure that may be carried out according to well known protocols.

In an embodiment, a Ferulac peel of the present disclosure may be used in combination with a radiofrequency treatment to enhance skin tightening, skin remodeling, and skin rejuvenation. In an embodiment, a Ferulac peel of the present disclosure may be applied before radiofrequency therapy to enhance the results of radiofrequency therapy. In an embodiment, a Ferulac peel of the present disclosure may be applied subsequent to radiofrequency therapy to enhance post-treatment healing.

Microdermabrasion

Microdermabrasion applies light mechanical abrasion from jets of fine organic particles or a rough surface to partially or completely remove dead skin cells on the skin surface. Microdermabrasion has been used to treat acne and melasma. Microdermabrasion is a common cosmetic procedure that may be carried out according to well known protocols.

In an embodiment, a Ferulac peel of the present disclosure may be used in combination with a microdermabrasion treatment to enhance skin rejuvenation and skin healing. In an embodiment, a Ferulac peel of the present disclosure may be used prior to microdermabrasion treatment to enhance the microdermabrasion results. In particular, it is believed that pre-microdermabrasion application of a Ferulac peel of the present disclosure may lead to faster results and more complete results, as well as skin color improvement. In an embodiment, a Ferulac peel of the present disclosure may be applied following a microdermabrasion procedure treatment to enhance post-treatment healing.

Electroporation

Electroporation is a well known procedure that may be carried out according to well established protocols to enhance molecular penetration of chemicals into the skin by application of an electromagnetic pulse. In an embodiment, a Ferulac peel of the present disclosure may be used in combination with electroporation to enhance penetration of the peel active ingredients by corneocyte cohesion, and by altering the lipidic membranes.

Iontophoresis

Iontophoresis helps deliver water-soluble compositions deep into the epidermis where melanin may be localized, and into the derma where collagen and elastin synthesis occur. Iontophoresis is a well known procedure which may be carried out according to well established protocols by those of ordinary skill in the art. In an embodiment, a Ferulac peel of the present disclosure may be used in combination with iontophoresis to enhance penetration of the peel active ingredients into the epidermis and derma to enhance clinical results of the Ferulac peel.

Ultrasound

Ultrasound uses low-frequency sound waves for mechanical exfoliation and molecular penetration. It is believed that ultrasound promotes collagen production, improves skin tone, and increases skin elasticity. Ultrasound is a common medical procedure and may be carried out according to well known protocols by those having ordinary skill in the art. In an embodiment, a Ferulac peel of the present disclosure may be combined with ultrasound treatment to enhance penetration of the peel actives and synergistically improve exfoliation.

In an embodiment, the present disclosure provides respective kit assemblies or "treatment kits" for treating the respective skin conditions set forth above. In an embodiment, each respective kit assembly is prepackaged to contain the appropriate topical agents and supplies, and includes an effective and convenient instructional means, such as an instructional pamphlet or a videotape or other instructional means containing thereon indicia for administration of sequentially applied products according to steps needed for the respective skin condition to be treated.

In an embodiment, the kit assembly also provides a sequential dispenser means containing a plurality of daily sets of kit sub-assembly components, such as a series of jars, bottles, containers or ampoules containing a supply (unit dose) of chemical solution. In addition to respective kits being specific for treatment of each aforementioned skin condition, kits are further respectively specific with regard to whether a given kit is to be used for the therapeutic phase or, in the alternative, for a maintenance phase.

Generally, and except as set forth for specific skin conditions, each kit provided in the present disclosure has sub-assembly components including therein the following: a unit dose of a booster product in a first container comprising ferulic acid and phloretin in a mixture of ethanol and macrogol; a unit dose of at least one exfoliating product in a second container comprising ferulic acid and phloretin in a mixture of ethanol and macrogol; and a unit dose of a nano-additive product in a third container comprising ferulic acid and phloretin encapsulated in liposomes. In an embodiment, a concentration of ferulic acid in the booster product is about 12% and a concentration of ferulic acid in the exfoliating product is about 8%. In an embodiment, the exfoliating product further comprises at least one of fruit acids or alpha hydroxyacids. In an embodiment, the nano-additive product further includes at least one of azelaic acid, nicotinic acid, retinol, and ceramides.

EXAMPLES

The following examples are illustrative of the benefits of practicing the systems and methods of the presently disclosed embodiments when applying an antioxidant peel.

Example 1

Figure 5:
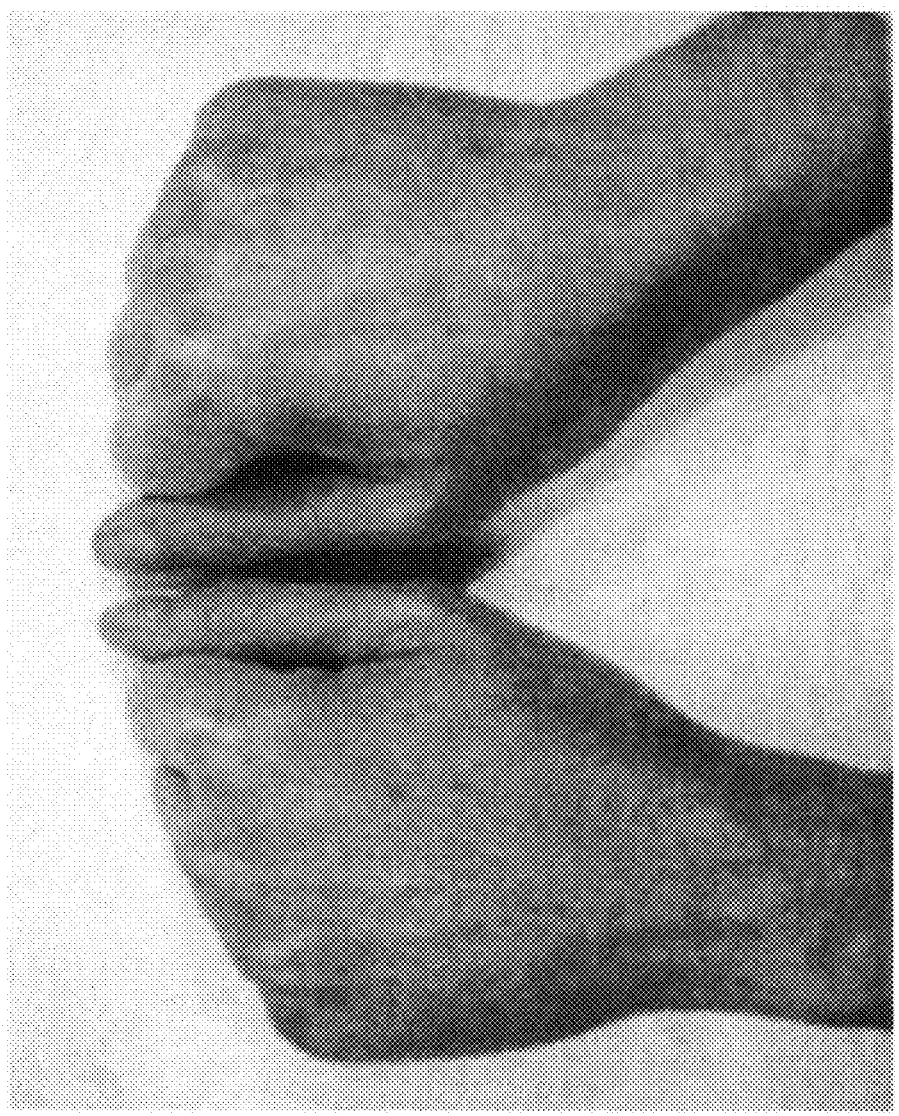
FIG. 5 is a photograph showing a comparison between the left (non treated) hand and the improvement of sun spots on the right hand of a patient treated with an embodiment of a Ferulac Classic peel (2 coats) of the present disclosure.

FIG. 5 shows a comparison between the left hand (not treated) and the right hand of an individual treated with a Ferulac Classic peel of the present disclosure applied twice with a one week interval in between. As shown in FIG. 5, improvement in color and sun spots on the right hand is noted.

Example 2

FIG. 6A shows a patient with extensive sun damage of the V of the neck before receiving a Ferulac peel of the present disclosure. FIG. 6B shows improved color and reduced sun spotting on the patient shown in FIG. 6A after two applications of a Ferulac peel of the present disclosure at one week interval in between treatments.

Example 3

Figure 7:
FIG. 7 is a collage of photographs showing a patient's reduced acne lesions and smoothing of scars after a series of treatments with an embodiment of a Ferulac peel of the present disclosure.

As shown in FIG. 7, Ferulac classic (2 coats) and Ferulac plus (2 coats) were applied every 2 weeks for a series of three treatments. As evident in FIG. 7, acne lesions notably reduced and the scars begin to smooth.

Example 4

Figure 8C:
FIG. 8B and FIG. 8C are photographs of a whitish mask developed on the skin of the patient shown in FIG. 8A as a result of evaporation of the ethanol and crystallization of the active ingredients after application of two coats of Ferulac classic and one coat of Ferulac plus.
Figure 8B:
Figure 8A:
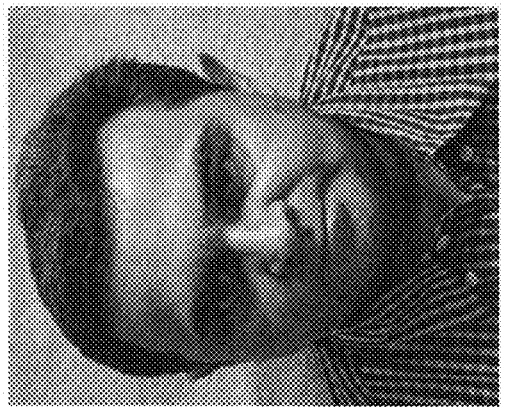
FIG. 8A is a photograph showing a patient before receiving an embodiment of a Ferulac peel of the present disclosure. The Ferulac peel includes ferulic acid and phloretin in a mixture of ethanol and macrogol.

FIG. 8A shows a patient before receiving a Ferulac peel treatment of the present disclosure. FIG. 8B and FIG. 8C show the patient in FIG. 8A after application of two coats of Ferulac classic and one coat of Ferulac plus. As illustrated in FIG. 8B and FIG. 8C, a whitish mask developed on the skin by evaporation of the ethanol vehicle and crystallization of the active ingredients.

Formulations or compositions that can be used with a Ferulac peel system of the present disclosure may include, but are not limited to, antioxidants, chelating agents, emollients, emulsifiers, humectants, surfactants, viscosity modifiers, natural moisturizing factors, antimicrobial actives, pH modifiers, enzyme inhibitors/inactivators, suspending agents, pigments, dyes, colorants, buffers, perfumes, antibacterial actives, antifungal actives, pharmaceutical actives, film formers, deodorants, skin conditioners, opacifiers, astringents, solvents, organic acids, preservatives, drugs, vitamins, aloe vera, and the like.

In an embodiment, the present disclosure is a step-by-step cosmetic skin-care system that includes several products which may be used in a particular order.

A system for skin rejuvenation includes a booster product for activating a skin area to be treated; at least one exfoliating product for exfoliating the skin area; and a nano-additive product for enhancing penetration of the booster product and the exfoliating product inside the skin area. In an embodiment, the system is a chemical peel system. In an embodiment, the chemical peel system is a ferulic acid (FA) chemical peel system. In an embodiment, the FA chemical peel system is an antioxidant based peel.

A skin rejuvenation system includes a unit dose of a booster product in a first container for activating a skin area to be treated; a unit dose of at least one exfoliating product in a second container for exfoliating the skin area; and a unit dose of a nano-additive product in a third container for enhancing penetration of the booster product and the exfoliating product inside the skin area. In an embodiment, the skin rejuvenation system is a chemical peel system. In an embodiment, the chemical peel system is a ferulic acid (FA) chemical peel system. In an embodiment, the FA chemical peel system is an antioxidant based peel.

A skin rejuvenation system includes a unit dose of a booster product in a first container for activating a skin area to be treated, the booster product comprising ferulic acid and phloretin in a dermatologically acceptable carrier; a unit dose of at least one exfoliating product in a second container for exfoliating the skin area, the exfoliating product comprising ferulic acid and phloretin in a dermatologically acceptable carrier; and a unit dose of a nano-additive product in a third container for enhancing penetration of the booster product and the exfoliating product inside the skin area, the nano-additive product comprising ferulic acid and phloretin in liposomes. In an embodiment, the skin rejuvenation system is a ferulic acid (FA) chemical peel system. In an embodiment, the FA chemical peel system is an antioxidant based peel.

A skin rejuvenation kit includes a unit dose of a booster product in a first container comprising ferulic acid and phloretin in a mixture of ethanol and macrogol; a unit dose of at least one exfoliating product in a second container comprising ferulic acid and phloretin in a mixture of ethanol and macrogol; and a unit dose of a nano-additive product in a third container comprising ferulic acid and phloretin encapsulated in liposomes. In an embodiment, the nano-additive product further includes at least one of azelaic acid, nicotinic acid, retinol, and ceramides. In an embodiment, a concentration of ferulic acid in the exfoliating product is less than a concentration of ferulic acid in the booster product. In an embodiment, the liposomal lipid is a phosphatidylcholine (PC).

An antioxidant based peel includes a unit dose of an activating product, the activating product including active ingredients of ferulic acid and phloretin in a mixture of ethanol and macrogol; a unit dose of at least one exfoliating product, the exfoliating product including active ingredients of ferulic acid and phloretin in combination with one of fruit acids or alpha hydroxyacids in a mixture of ethanol and macrogol; and a unit dose of an enhancing product, the enhancing product including active ingredients of ferulic acid and phloretin in liposomes.

A skin rejuvenation system includes a booster product comprising ferulic acid and phloretin in a mixture of ethanol and macrogol; an exfoliating product in a mixture of ethanol and macrogol; and a nano-additive product comprising ferulic acid and phloretin encapsulated in phosphatidylcholine liposomes. In an embodiment, the exfoliating product includes ferulic acid, phloretin, a mixture of alpha hydroxyacids and a retinol. In an embodiment, the exfoliating product includes two or more polyphenolic acids. In an embodiment, the nano-additive product includes ferulic acid, phloretin, azelaic acid, nicotinic acid, retinol, and ceramides. In an embodiment, a concentration of ferulic acid in the exfoliating product is less than a concentration of ferulic acid in the booster product.

A method for skin rejuvenation includes applying topically to a skin surface to be treated a booster product for activating the skin, the booster product comprising active ingredients including ferulic acid and phloretin in a dermatologically acceptable carrier; applying topically to the skin surface at least one exfoliating product for exfoliating the skin, the exfoliating product comprising active ingredients including ferulic acid and phloretin in a dermatologically acceptable carrier; and applying topically to the skin surface a nano-additive product for enhancing penetration of the booster product and the exfoliating product into the skin, the nano-additive product comprising active ingredients including ferulic acid and phloretin in liposomes.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A system for treating skin comprising:
   a booster product comprising active ingredients including about 2% to about 15% ferulic acid and about 3% to about 10% phloretin in a dermatologically acceptable carrier;
   at least one exfoliating product comprising active ingredients including about 2% to about 15% ferulic acid and about 3% to about 10% phloretin in a dermatologically acceptable carrier, wherein a concentration of ferulic acid in the at least one exfoliating product is less than a concentration of ferulic acid in the booster product; and
   a nano-additive product for enhancing penetration of the booster product and the exfoliating product inside a skin area, the nano-additive product comprising active ingredients encapsulated in liposomes.

2. The system of claim 1, wherein the at least one exfoliating product further comprises retinol or a retinol derivative and a mixture of alpha hydroxyacids.

3. The system of claim 1, wherein the at least one exfoliating product further comprises at least one of caffeic acid, rosmarinic acid, lactic acid, or trichloroacetic acid.

4. The system of claim 1, wherein the active ingredients in the nano-additive product include ferulic acid and phloretin.

5. The system of claim 1, wherein the active ingredients in the nano-additive product further include at least one of azelaic acid, nicotinic acid, retinol, or ceramides.

6. The system of claim 1, further comprising an oxygen product for increasing an oxygen content to the skin area.

7. The system of claim 1, further comprising a Vitamin C product for ameliorating symptoms associated with photoaging of the skin area.

8. The system of claim 1, wherein the system is used for skin rejuvenation.

9. A skin treatment kit comprising:
   a unit dose of a booster product in a first container, the booster product comprising about 2% to about 15% ferulic acid and about 3% to about 10% phloretin in a mixture of ethanol and macrogol;
   a unit dose of at least one exfoliating product in a second container, the exfoliating product comprising about 2% to about 15% ferulic acid and about 3% to about 10% phloretin in a mixture of ethanol and macrogol, wherein a concentration of ferulic acid in the at least one exfoliating product is less than a concentration of ferulic acid in the booster product; and
   a unit dose of a nano-additive product in a third container, the nano-additive product comprising ferulic acid and phloretin encapsulated in liposomes.

10. The kit of claim 9, wherein the at least one exfoliating product further comprises at least one of caffeic acid, rosmarinic acid, lactic acid, or trichloroacetic acid.

11. The kit of claim 9, wherein the at least one exfoliating product further comprises fruit acids or alpha hydroxyacids.

12. The kit of claim 9, wherein the nano-additive product further comprises at least one of azelaic acid, nicotinic acid, retinol, or ceramides.

13. A method for treating skin comprising:
   applying topically to a skin surface to be treated a booster product comprising active ingredients including about 2% to about 15% ferulic acid and about 3% to about 10% phloretin in a dermatologically acceptable carrier;
   applying topically to the skin surface at least one exfoliating product comprising active ingredients including about 2% to about 15% ferulic acid and about 3% to about 10% phloretin in a dermatologically acceptable carrier, wherein a concentration of ferulic acid in the at least one exfoliating product is less than a concentration of ferulic acid in the booster product; and
   applying topically to the skin surface a nano-additive product for enhancing penetration of the booster product and the at least one exfoliating product into the skin, the nano-additive product comprising active ingredients including ferulic acid and phloretin encapsulated in liposomes.

14. The method of claim 13, wherein the at least one exfoliating product further comprises fruit acids or alpha hydroxyacids.

15. The method of claim 13, wherein the at least one exfoliating product further comprises retinol or a retinol derivative and a mixture of alpha hydroxy acids.

16. The method of claim 13, wherein the at least one exfoliating product further comprises at least one of caffeic acid, rosmarinic acid, lactic acid, or trichloroacetic acid.

17. The method of claim 13, wherein the active ingredients in the nano-additive product further includes at least one of azelaic acid, nicotinic acid, retinol, or ceramides.

18. The method of claim 13, further comprising applying topically to the skin surface an oxygen product for increasing an oxygen content of the skin.

19. The method of claim 13, further comprising applying topically to the skin surface a Vitamin C product for ameliorating symptoms associated with photo-aging of the skin.

20. The method of claim 13, further comprising applying topically to the skin surface a protectant for protecting the skin from photo-damaging conditions.

21. The method of claim 13, further comprising performing a skin rejuvenation treatment on the skin surface, wherein the skin rejuvenation treatment comprises intense pulsed light, light emitting diodes, laser therapy, light resurfacing therapy, radiofrequency, photodynamic therapy, dermabrasion, microdermabrasion, electroporation, iontophoresis, or ultrasound, or combinations thereof.

* * * * *